(12) United States Patent
Barry

(10) Patent No.: US 8,986,356 B2
(45) Date of Patent: Mar. 24, 2015

(54) UNIPLANAR BONE ANCHOR SYSTEM

(71) Applicant: EBI, LLC, Parsippany, NJ (US)

(72) Inventor: David Barry, Teaneck, NJ (US)

(73) Assignee: EBI, LLC, Parsippany, NJ (US)

( * ) Notice: Subject to any disclaimer, the term of this patent is extended or adjusted under 35 U.S.C. 154(b) by 44 days.

(21) Appl. No.: 13/803,221

(22) Filed: Mar. 14, 2013

(65) Prior Publication Data

US 2013/0204308 A1    Aug. 8, 2013

Related U.S. Application Data

(62) Division of application No. 12/688,013, filed on Jan. 15, 2010, now Pat. No. 8,419,778.

(51) Int. Cl.
*A61B 17/86*    (2006.01)
*A61B 17/70*    (2006.01)

(52) U.S. Cl.
CPC ......... *A61B 17/8605* (2013.01); *A61B 17/7037* (2013.01); *A61B 17/7038* (2013.01); *A61B 17/7032* (2013.01)
USPC ............................ 606/306; 606/305; 606/308

(58) Field of Classification Search
CPC ........... A61B 17/8685; A61B 17/8605; A61B 17/86; A61B 17/84; A61B 17/7035; A61B 17/7038
USPC .................................................. 606/305–308
See application file for complete search history.

(56) References Cited

U.S. PATENT DOCUMENTS

| | | | |
|---|---|---|---|
| 4,653,481 A | 3/1987 | Howland et al. |
| 4,987,892 A | 1/1991 | Krag et al. |
| 5,190,543 A | 3/1993 | Schlapfer |
| 5,261,909 A | 11/1993 | Sutterlin et al. |
| 5,499,983 A | 3/1996 | Hughes |
| 5,989,254 A | 11/1999 | Katz |
| 6,800,079 B2 | 10/2004 | Reed |

(Continued)

FOREIGN PATENT DOCUMENTS

| | | |
|---|---|---|
| EP | 1923011 A1 | 5/2008 |
| WO | 2007011407 A1 | 1/2007 |

OTHER PUBLICATIONS

European Search Report and Written Opinion Dated Oct. 31, 2011 for EP11005286.

(Continued)

*Primary Examiner* — Eduardo C Robert
*Assistant Examiner* — Julianna N Harvey
(74) *Attorney, Agent, or Firm* — Harness, Dickey

(57) ABSTRACT

The present teachings provide one or more surgical implements for repairing damaged tissue, such as in the case of a spinal fixation procedure. A uniplanar bone anchor system for a fixation procedure is provided. The system can include a bone fastener including a head with a bearing surface and a shaft adapted to engage an anatomy. The system can also include a saddle, which can include a first bore formed about a longitudinal axis that receives the bone fastener and a coupling bore defined transverse to the longitudinal axis. The system can also include a coupling system, which can have a second bearing surface. The coupling system can be received through the coupling bore such that the second bearing surface of the coupling system can contact the bearing surface to permit the bone fastener to move in only one plane.

12 Claims, 23 Drawing Sheets

(56) References Cited

U.S. PATENT DOCUMENTS

| | | |
|---|---|---|
| 7,314,467 B2 | 1/2008 | Howland |
| 7,766,944 B2 | 8/2010 | Metz-Stavenhagen |
| 7,850,718 B2 | 12/2010 | Bette et al. |
| 8,419,778 B2 | 4/2013 | Barry |
| 2005/0080420 A1 | 4/2005 | Farris et al. |
| 2006/0089644 A1 | 4/2006 | Felix |
| 2006/0111715 A1 | 5/2006 | Jackson |
| 2006/0155277 A1 | 7/2006 | Metz-Stavenhagen |
| 2006/0200131 A1* | 9/2006 | Chao et al. ............ 606/61 |
| 2007/0043355 A1 | 2/2007 | Bette et al. |
| 2007/0088357 A1* | 4/2007 | Johnson et al. ........ 606/61 |
| 2007/0161966 A1 | 7/2007 | West et al. |
| 2007/0161996 A1 | 7/2007 | Biedermann et al. |
| 2008/0077138 A1 | 3/2008 | Cohen et al. |
| 2008/0147129 A1 | 6/2008 | Biedermann et al. |
| 2008/0161859 A1 | 7/2008 | Nilsson |
| 2008/0161863 A1* | 7/2008 | Arnold et al. ......... 606/319 |
| 2008/0183223 A1 | 7/2008 | Jeon et al. |
| 2008/0195159 A1 | 8/2008 | Kloss et al. |
| 2008/0234757 A1 | 9/2008 | Jacofsky et al. |
| 2008/0234759 A1 | 9/2008 | Marino |
| 2008/0249570 A1 | 10/2008 | Carson et al. |
| 2008/0306553 A1 | 12/2008 | Zucherman et al. |
| 2009/0076552 A1 | 3/2009 | Tornier |
| 2009/0105769 A1 | 4/2009 | Rock et al. |
| 2009/0198280 A1 | 8/2009 | Spratt et al. |
| 2010/0094343 A1 | 4/2010 | Pham et al. |
| 2010/0305621 A1 | 12/2010 | Wang et al. |
| 2011/0106173 A1 | 5/2011 | Lindemann et al. |
| 2011/0106174 A1 | 5/2011 | Rezach |
| 2011/0178559 A1 | 7/2011 | Barry |

OTHER PUBLICATIONS

European Office Action, dated Jan. 31, 2013 for Application No. 11 005 286.7 filed Jun. 29, 2011.

European Office Action—Intent to Grant, dated Jul. 5, 2013 for Application No. 11 005 286.7 filed Jun. 29, 2011.

\* cited by examiner

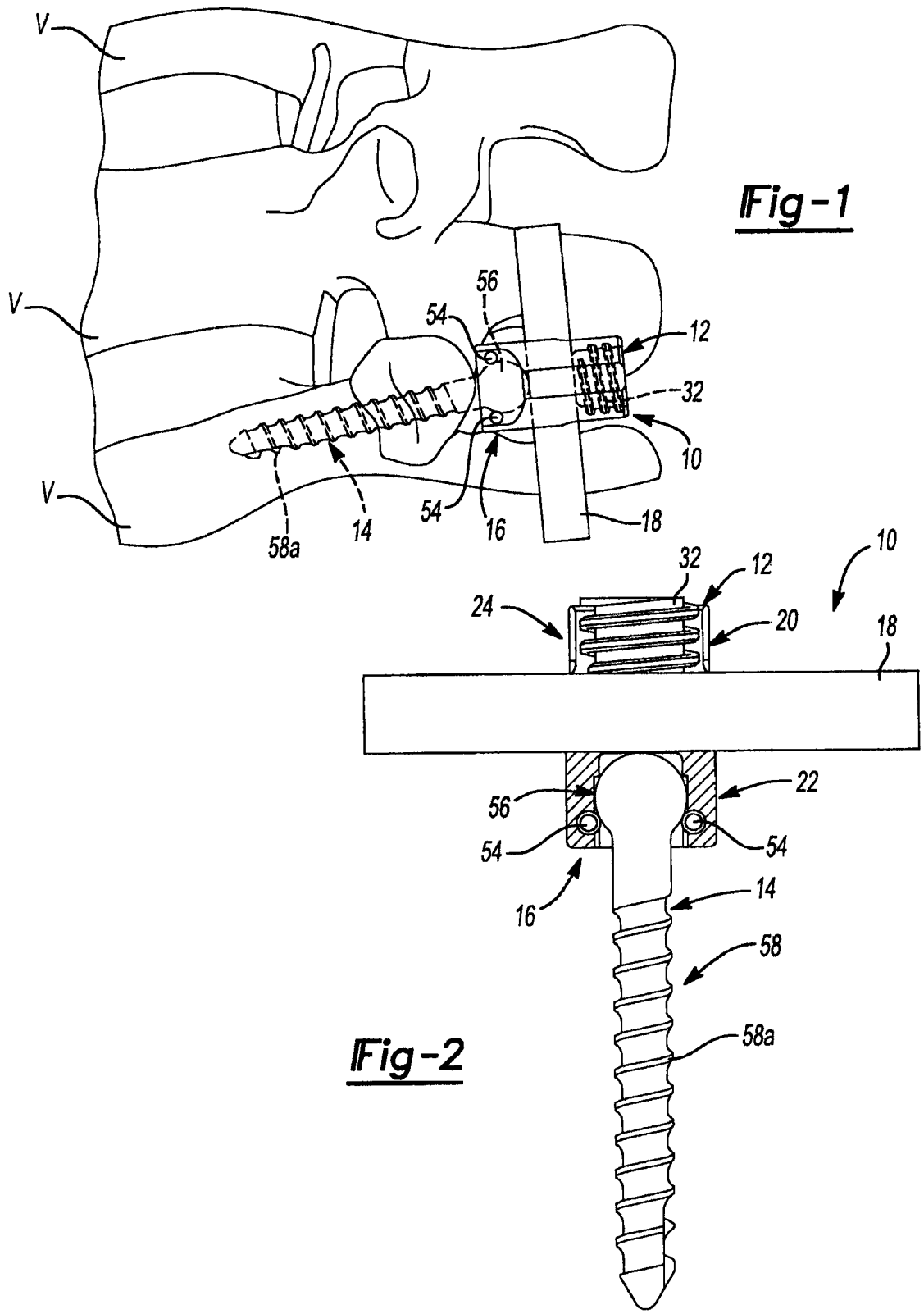

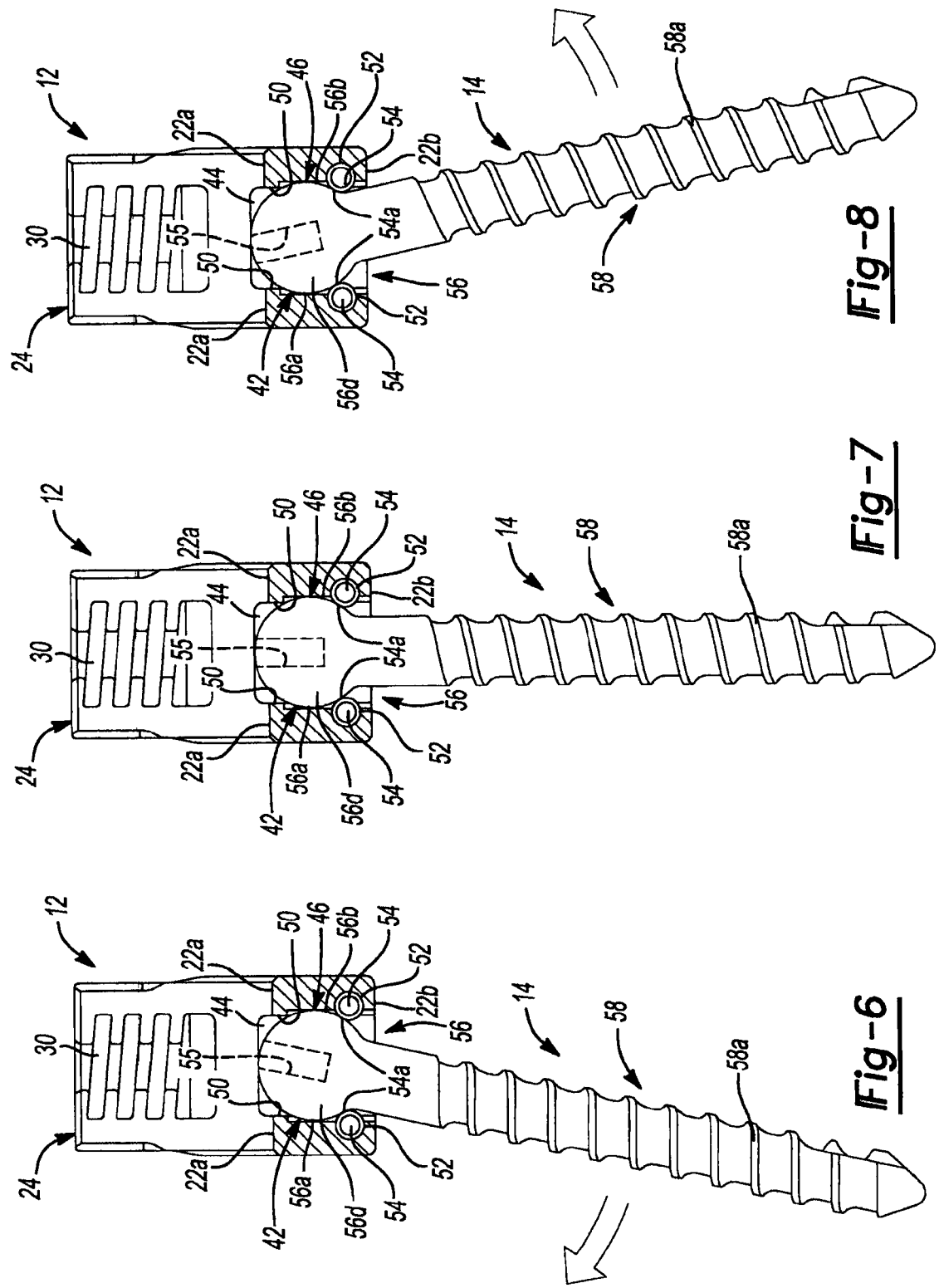

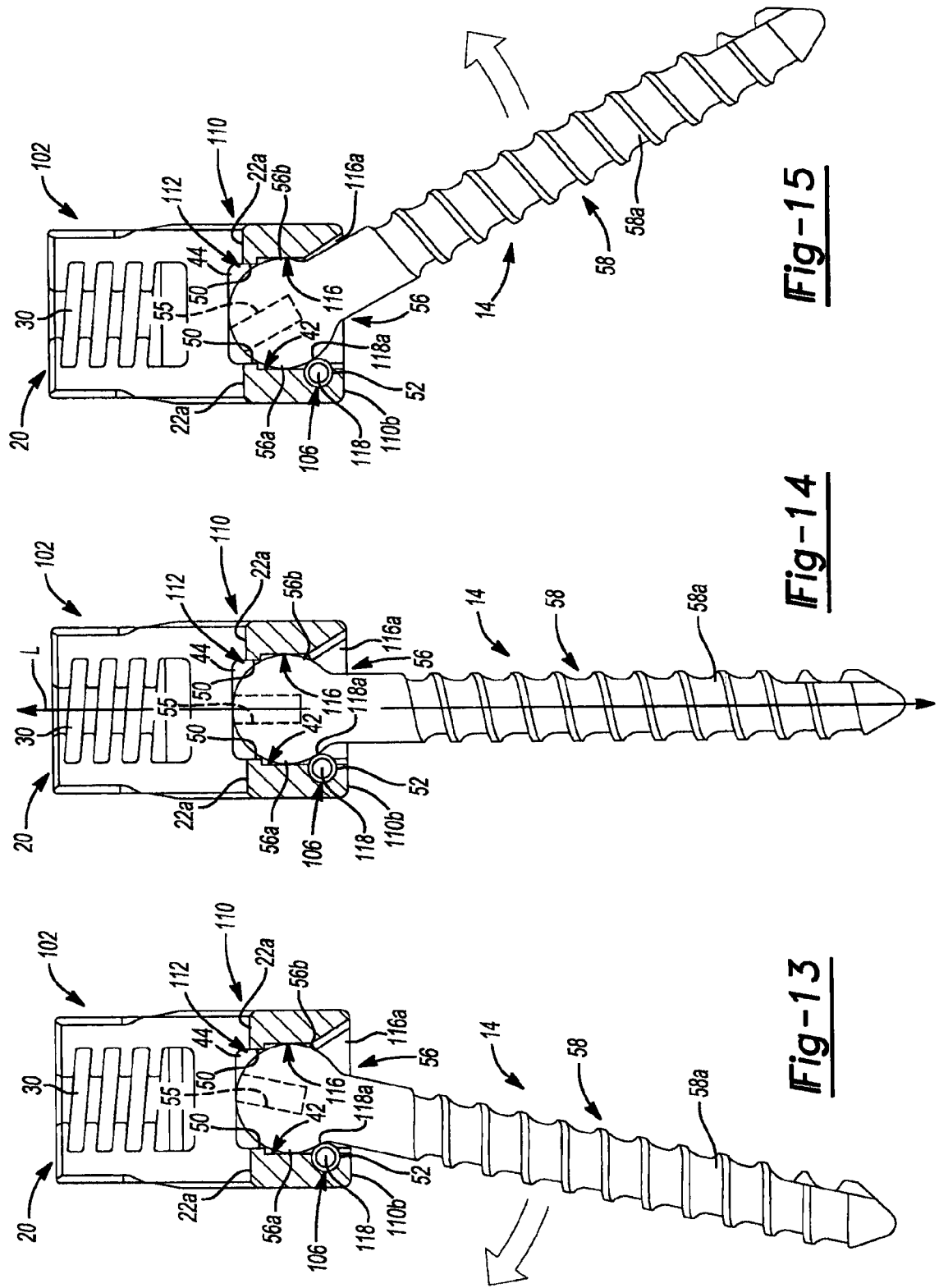

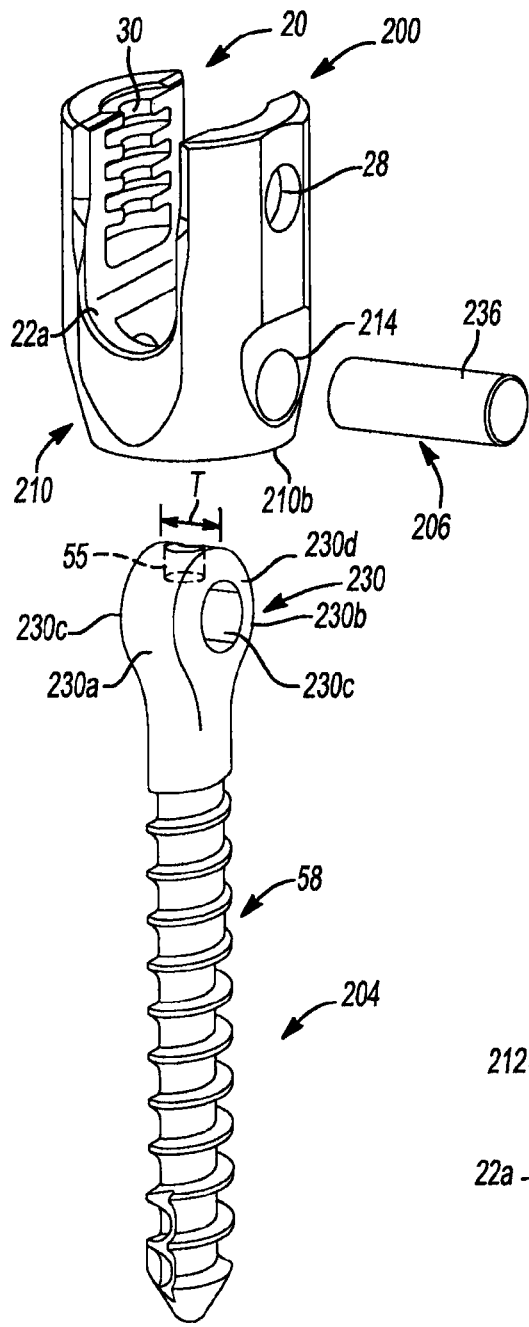
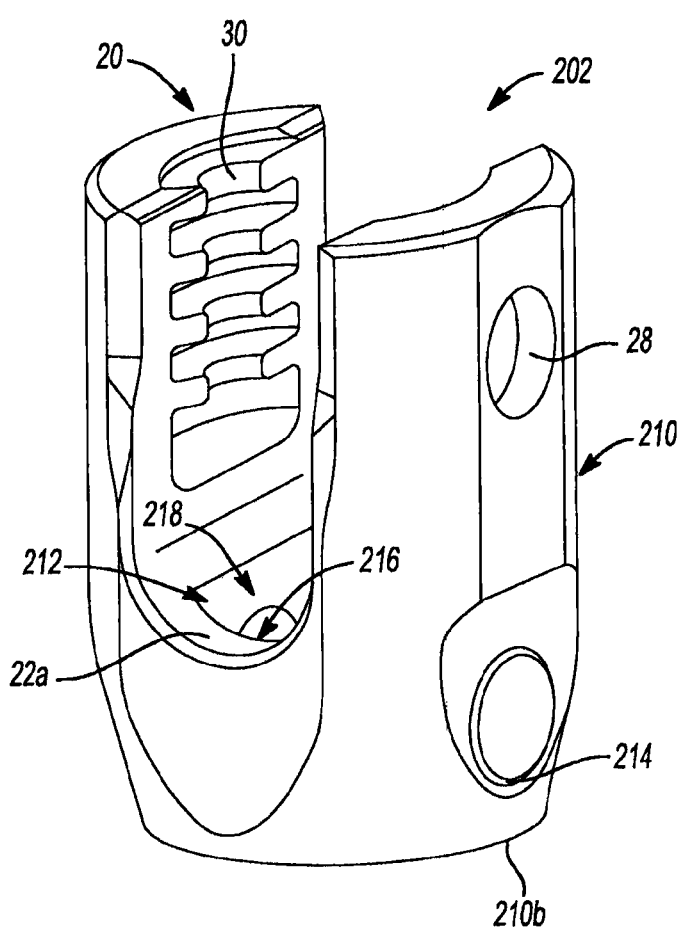
Fig-18
Fig-19

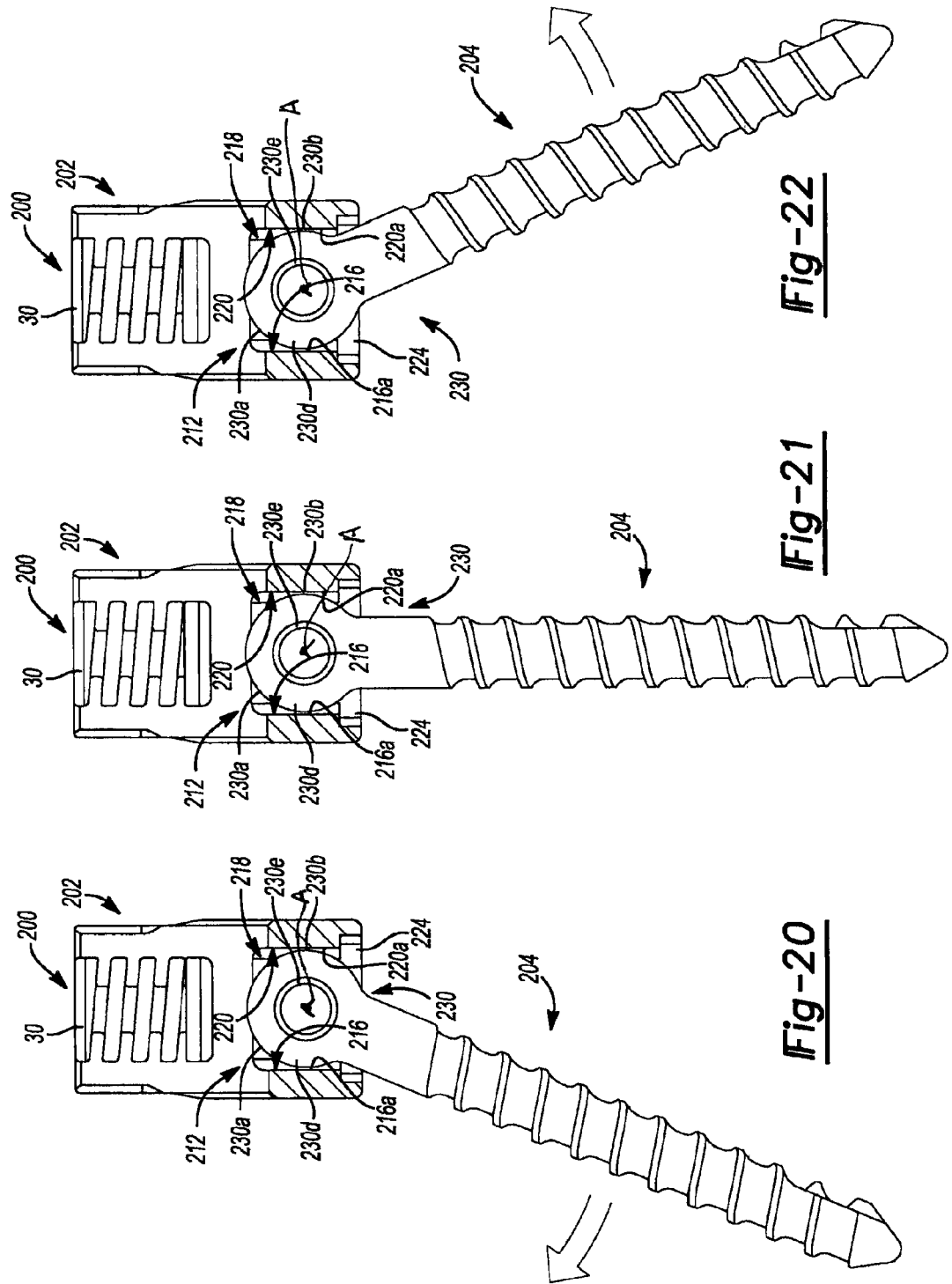

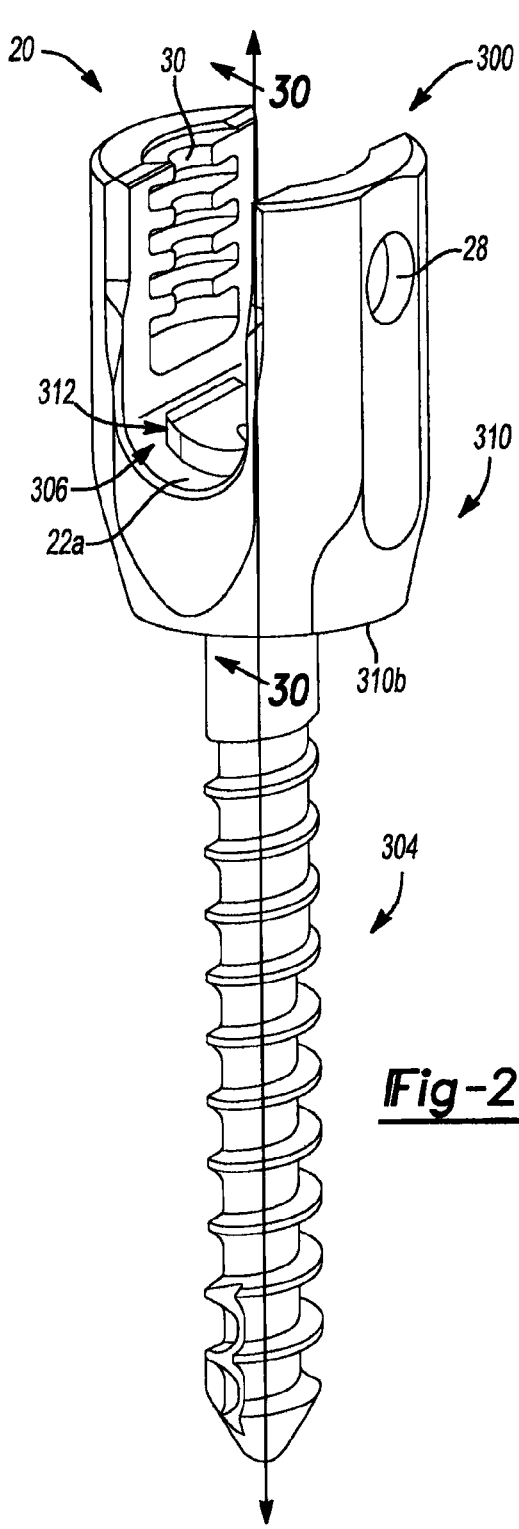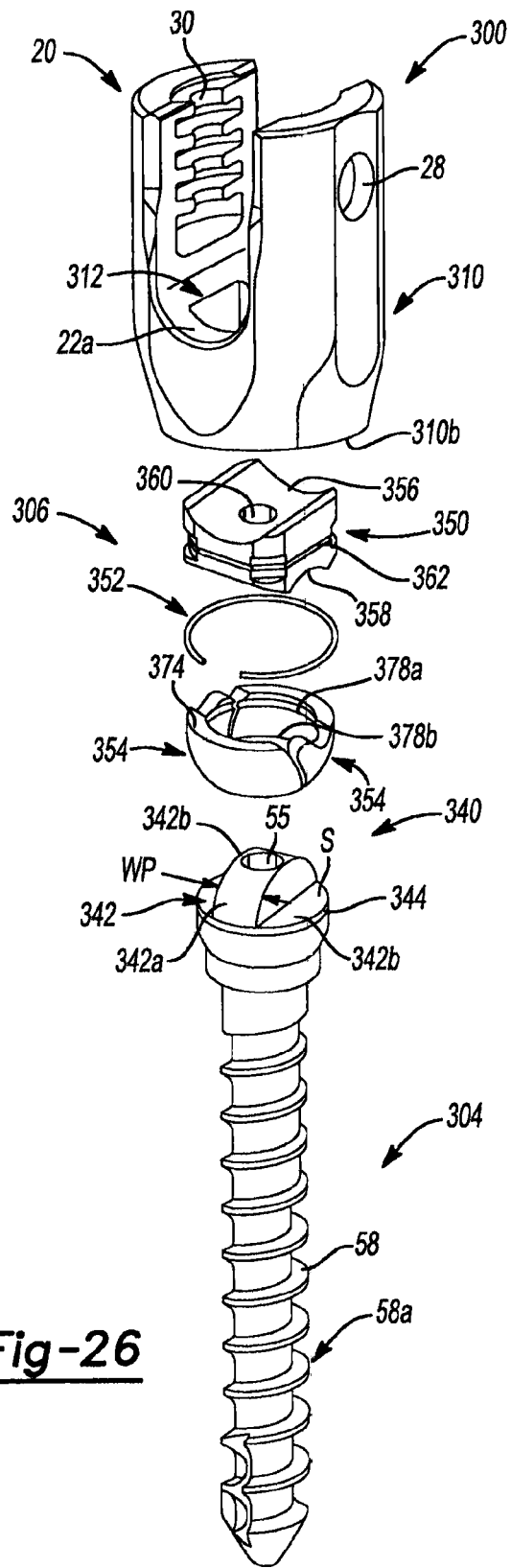
Fig-25
Fig-26

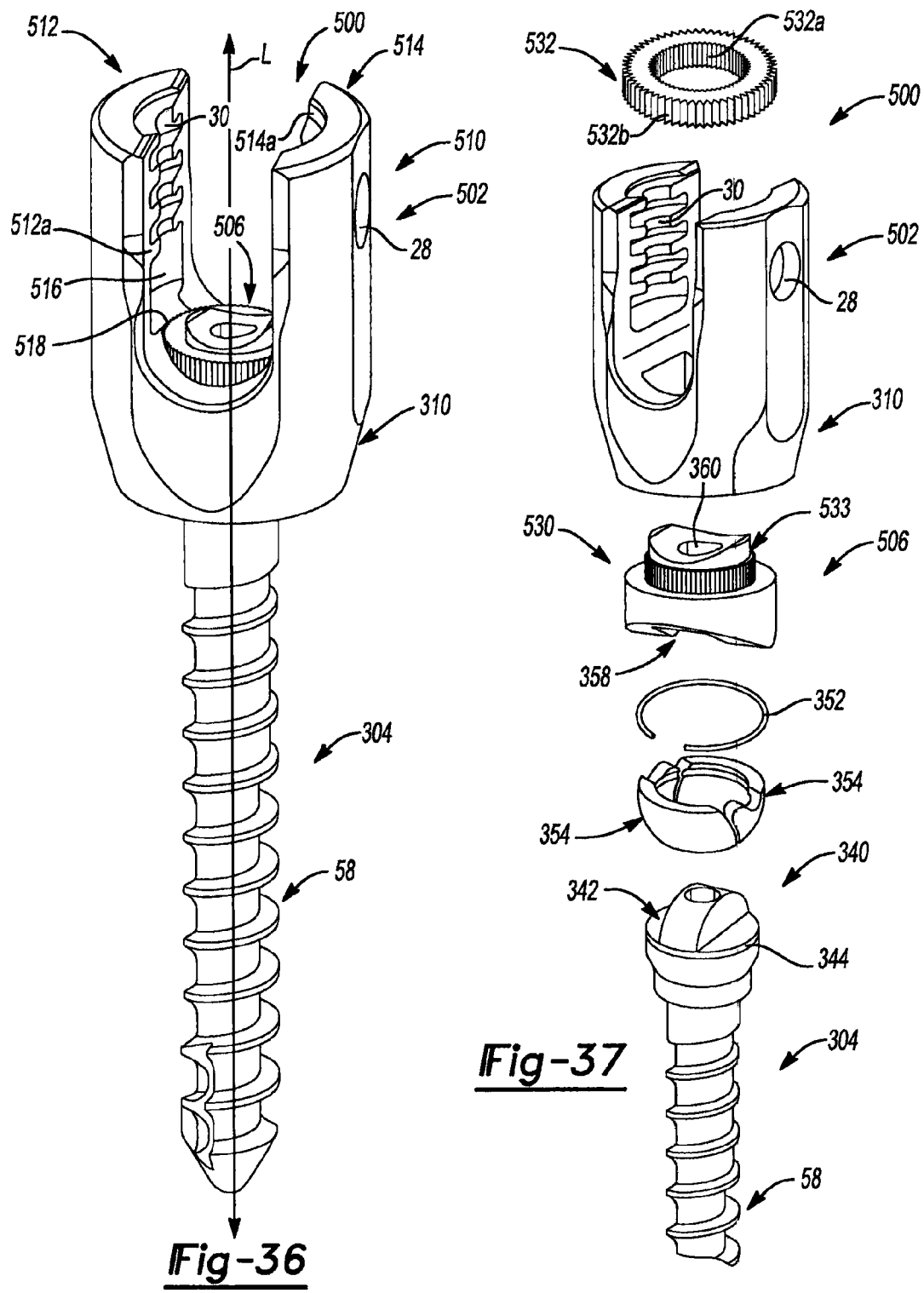

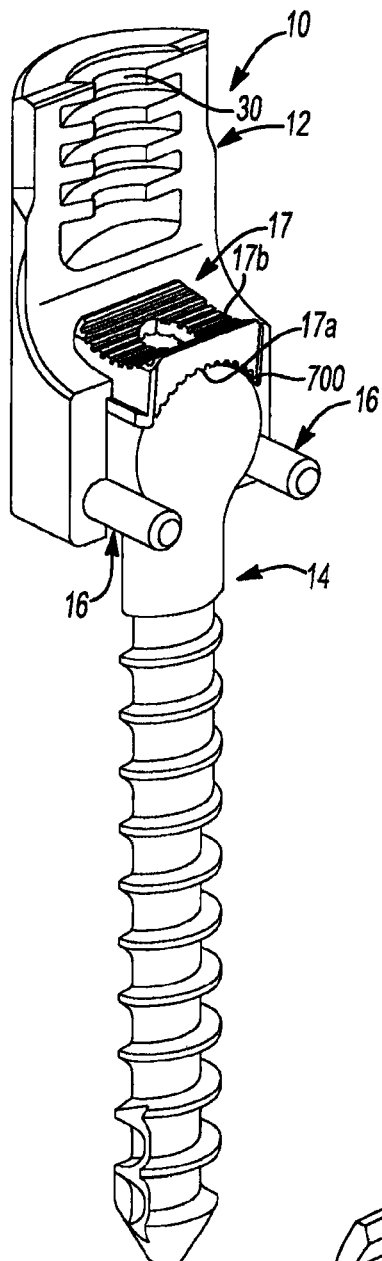
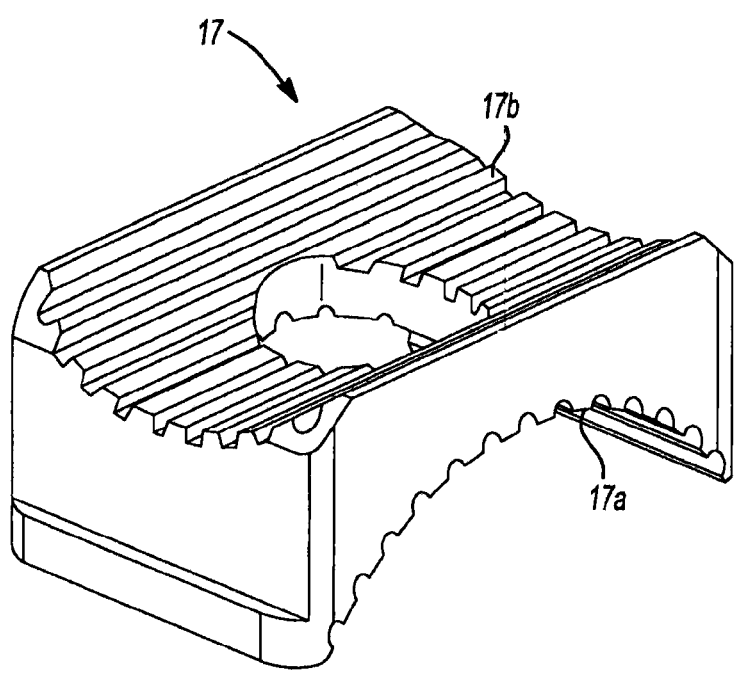
Fig-48
Fig-47

UNIPLANAR BONE ANCHOR SYSTEM

CROSS-REFERENCE TO RELATED APPLICATIONS

This application is a divisional of U.S. patent application Ser. No. 12/688,013 filed on Jan. 15, 2010. The entire disclosure of the above application is incorporated herein by reference.

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged or deformed tissue, which can require the use of one or more orthopedic prosthesis, such as orthopedic nails, screws, implants, etc., to restore function to the damaged tissue.

Generally, in order to stabilize various boney tissue relative to one another, such as vertebrae of the spine, one or more implants can be coupled to each of the vertebrae and interconnected via a suitable device. In one example, implants or anchors can be coupled to each of the vertebrae, and a connecting device, such as a rod, can be coupled to each of the anchors to stabilize or fix the vertebrae relative to each other. In certain instances, it may be desirable to provide an anchor that can move relative to the connecting device. The present teachings can provide an anchor for use in repairing damaged or deformed tissue, such as a bone anchor that can be movable in only one plane for use in a fixation procedure.

Provided is a uniplanar bone anchor system for a fixation procedure. The system can include a bone fastener including a head and a shaft adapted to engage an anatomy. The head can have a bearing surface. The system can also include a saddle, which can extend along a longitudinal axis. The saddle can have a proximal end and a distal end. The distal end of the saddle can include a first bore formed about the longitudinal axis that receives the head of the bone fastener and at least one coupling bore defined transverse to the longitudinal axis through at least a portion of the distal end. The at least one coupling bore can be in communication with the first bore. The system can also include a coupling system, which can have at least one second bearing surface. The coupling system can be received through the at least one coupling bore such that the at least one second bearing surface of the coupling system can contact the bearing surface of the head to permit the bone fastener to move relative to the saddle in only one plane.

Further provided is a uniplanar bone anchor system for a fixation procedure. The system can include a bone fastener including a head and a shaft adapted to engage an anatomy. The head can have at least one first bearing surface. The system can also include a saddle having a proximal end and a distal end. The distal end of the saddle can include a first bore formed about the longitudinal axis, which can receive the head of the bone fastener. The system can comprise a coupling system, which can include a cap and at least one annular support. The cap can define at least one second bearing surface configured to allow the bone fastener to move in one plane relative to the saddle. The at least one annular support can be coupled to the head of the bone fastener to retain the bone fastener within the first bore. The cap can be received within the first bore such that the at least one second bearing surface of the cap contacts the at least one first bearing surface of the head to permit the bone fastener to move relative to the saddle in one plane.

Also provided is a uniplanar bone anchor system for a fixation procedure. The system can include a bone fastener having a head and a shaft adapted to engage an anatomy. The head can have a first bearing surface opposite a second bearing surface. The system can also include a saddle extending along a longitudinal axis. The saddle can have a proximal end and a distal end. The distal end can include a first bore formed about the longitudinal axis that receives the head of the bone fastener. The distal end can also include a first sidewall opposite a second sidewall. A first coupling bore can be defined transverse to the longitudinal axis through at least a portion of the distal end. A second coupling bore can be defined transverse to the longitudinal axis through at least a portion of the distal end. The first coupling bore and the second coupling bore can be spaced a distance apart from each other and in communication with the first bore. The system can also include a first coupling pin, which can be positionable within the first coupling bore. The first coupling pin can define a third bearing surface in communication with the first bore. The system can include a second coupling pin. The second coupling pin can be positionable within the second coupling bore, and can define a fourth bearing surface in communication with the second bore. The bone fastener can be received within the first bore such that the first bearing surface of the head can contact the third bearing surface of the first coupling pin, and the second bearing surface of the head can contact the fourth bearing surface of the second coupling pin to enable the bone fastener to articulate relative to the saddle in a single plane.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 1 is a schematic environmental illustration of an exemplary uniplanar bone anchor system for use with a connecting device in a fixation procedure according to the present teachings;

FIG. 2 is a schematic cross-sectional illustration of the uniplanar bone anchor system of FIG. 1;

FIG. 6 is a schematic, cross-sectional illustration of the uniplanar bone anchor system, taken along line 6-6 of FIG. 3, which illustrates a first direction of uniplanar motion for the uniplanar bone anchor system;

FIG. 7 is a schematic, cross-sectional illustration of the uniplanar bone anchor system, taken along line 6-6 of FIG. 3, which illustrates a neutral position for the uniplanar bone anchor system;

FIG. 8 is a schematic, cross-sectional illustration of the uniplanar bone anchor system, taken along line 6-6 of FIG. 3, which illustrates a second direction of uniplanar motion for the uniplanar bone anchor system;

FIG. 13 is a schematic, cross-sectional illustration of the uniplanar bone anchor system, taken along line 13-13 of FIG. 12, which illustrates a first direction of uniplanar motion for the uniplanar bone anchor system;

FIG. 14 is a schematic, cross-sectional illustration of the uniplanar bone anchor system, taken along line 13-13 of FIG. 12, which illustrates a neutral position for the uniplanar bone anchor system;

FIG. 15 is a schematic, cross-sectional illustration of the uniplanar bone anchor system, taken along line 13-13 of FIG. 12, which illustrates a second direction of uniplanar motion for the uniplanar bone anchor system;

FIG. 18 is an exploded view of the uniplanar bone anchor system of FIG. 16;

FIG. 19 is a perspective view of an exemplary saddle for use with the uniplanar bone anchor system of FIG. 16;

FIG. 20 is a schematic, cross-sectional illustration of the uniplanar bone anchor system, taken along line 20-20 of FIG. 17, which illustrates a first direction of uniplanar motion for the uniplanar bone anchor system;

FIG. 21 is a schematic, cross-sectional illustration of the uniplanar bone anchor system, taken along line 20-20 of FIG. 17, which illustrates a neutral position for the uniplanar bone anchor system;

FIG. 22 is a schematic, cross-sectional illustration of the uniplanar bone anchor system, taken along line 20-20 of FIG. 17, which illustrates a second direction of uniplanar motion for the uniplanar bone anchor system;

FIG. 25 is a schematic perspective illustration of another exemplary uniplanar bone anchor system for use with a connecting device in a fixation procedure according to the present teachings;

FIG. 26 is an exploded view of the uniplanar bone anchor system of FIG. 25;

FIG. 36 is a schematic perspective illustration of an exemplary uniplanar bone anchor system having a selectable single plane of motion for use with a connecting device in a fixation procedure according to the present teachings;

FIG. 37 is an exploded view of the uniplanar bone anchor system of FIG. 36;

FIG. 47 is another exemplary pressure cap for use with any of the exemplary bone anchor systems; and FIG. 48 is schematic cross-sectional illustration of another exemplary uniplanar bone anchor system for use with a connecting device in a fixation procedure according to the present teachings.

DESCRIPTION OF VARIOUS ASPECTS

Figure 3:
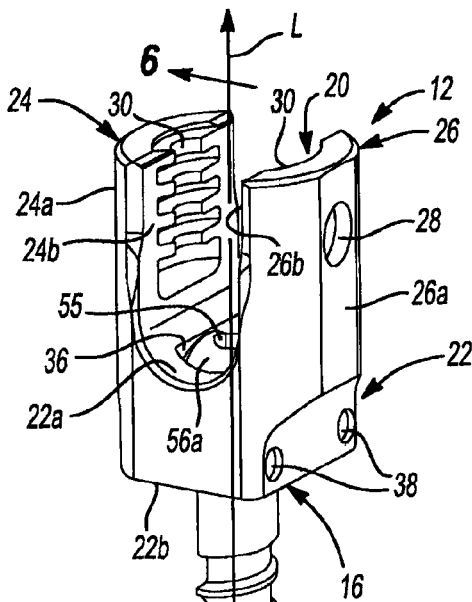
FIG. 3 is a perspective view of the uniplanar bone anchor system of FIG. 1.

The following description is merely exemplary in nature and is not intended to limit the present teachings, application, or uses. It should be understood that throughout the drawings, corresponding reference numerals indicate like or corresponding parts and features. Although the following description is related generally to a system for use in an anatomy to repair damaged tissue, such as in the case of spinal fusion, static spinal stabilization or dynamic spinal stabilization, it will be understood that the system as described and claimed herein can be used in any appropriate surgical procedure, such as in a minimally invasive orthopedic alignment or fixation procedure. Therefore, it will be understood that the following discussions are not intended to limit the scope of the present teachings and claims herein.

With reference to FIGS. 1-11, a uniplanar bone anchor system 10 is shown. The bone anchor system 10 may be particularly adapted for spinal fixation procedures. Various aspects of the present teachings, however, may have application for other procedures. In certain applications, the bone anchor system 10 can be coupled to one or more vertebrae or vertebral bodies V in a lumbar region of the spine, however, the bone anchor system 10 can be used in other anatomical locations. The bone anchor system 10 can include a tulip head or saddle 12 and a bone engaging member or bone fastener 14, which can be coupled together via a uniplanar coupling system 16. The uniplanar coupling system 16 can enable the saddle 12 to move relative to the bone fastener 14 in only a single plane. The bone anchor system 10 can also include a pressure cap 17 (FIGS. 9-11), if desired.

As will be discussed in greater detail herein, the saddle 12 can be configured to receive a connecting device or rod 18, which can be used to interconnect multiple bone anchor systems 10 (the same or different types) in an exemplary spinal fixation procedure. It should be noted, however, that although the bone anchor system 10 is generally illustrated and described herein as a single assembly for use with a single connecting rod 18, any combination of bone anchor systems 10 and connecting rods 18 can be employed during a surgical procedure.

For example, in a single level spinal fixation procedure, two bone anchor systems 10 can receive a single connecting rod 18. A multiple level spinal fixation procedure, however, will generally require additional bone anchor systems 10, which can include other types of bone anchor systems, such as those employing non-movable bone fasteners. In addition, the bone anchor systems 10 need not be coupled to adjacent vertebral bodies V, but rather, the bone anchor systems 10 can be positioned so as to skip adjacent vertebral bodies V, if desired.

With reference to FIGS. 3-8, the saddle 12 can be substantially U-shaped and symmetrical with respect to a longitudinal axis L defined by the bone anchor system 10. The saddle 12 can include a first or proximal end 20 and a second or distal end 22. In one example, the proximal end 20 can be integrally formed with the distal end 22 out of a suitable biocompatible material, however, the proximal end 20 and distal end 22 can be formed and coupled together through any suitable processing technique, such as machining and welding, etc. The proximal end 20 can include a first arm 24 and a second arm 26. The first arm 24 and second arm 26 can extend upwardly from the distal end 22 to define the U-shape. Each of the first arm 24 and the second arm 26 can include an insertion feature 28 and a mating portion 30.

The insertion feature 28 can enable the saddle 12 to be releasably coupled to a suitable instrument or tool for inserting and coupling the bone anchor system 10 to the anatomy. In one example, the insertion feature 28 can comprise a notch or groove formed on an exterior surface 24a, 26a of each of the first arm 24 and second arm 26. It should be noted, however, that the proximal end 20 can have any suitable configuration to engage a tool, such as keyed portions, chamfers, etc. Further, it should be noted that particular tools for use with the bone anchor system 10 are beyond the scope of the present teachings and need not be described herein. In a conventional manner insofar as the present teachings are concerned, various tools can be used to connect the bone anchor system 10 to a respective vertebral body V. Exemplary tools can include those employed in the Polaris™ 5.5 Spinal System, commercially available from Biomet, Inc. of Warsaw, Ind., or the tools disclosed in commonly owned U.S. Patent Publication No. 2008/0077138, filed on Apr. 20, 2007 and incorporated by reference herein.

The mating portion 30 can be configured to receive a fastening mechanism to couple or retain the connecting rod 18 within the saddle 12. For example, the mating portion 30 can comprise a plurality of threads, which can be formed on an interior surface 24b, 26b of each of the first arm 24 and second arm 26. In this example, the mating portion 30 can matingly engage threads formed on a set screw 32 to retain the connecting rod 18 within the saddle 12 (FIG. 2). It should be noted, however, that the proximal end 20 can have any suitable configuration to retain the connecting rod 18 to the saddle 12, such as keyed portions, teeth, etc.

With reference to FIGS. 3-8, the distal end 22 can be generally rectangular, and can include a first, top or a receiver surface 22a and a second or bottom surface 22b. It should be noted, however, that the distal end 22 can have any desired shape such as circular, octagonal, etc. In addition, the distal end 22 can include a central aperture or central bore 36 and at least one or more coupling apertures or coupling bores 38. The receiver surface 22a can provide clearance for the assembly of the connecting rod 18 to the saddle 12, but does not generally contact the connecting rod 18. In one example, the receiver surface 22a can comprise a generally arcuate, concave surface that forms the U-shape of the saddle 12, however, the receiver surface 22a can comprise any desired shape, such as square, etc.

The central bore 36 can be defined through the distal end 22 from the receiver surface 22a to the bottom surface 22b. Generally, the central bore 36 can be sized to receive the bone fastener 14, and can cooperate with the coupling system 16 to allow the bone fastener 14 to move in only one plane. With reference to FIGS. 5-8, the central bore 36 can include a first sidewall 42, a second sidewall 44, a third sidewall 46 and a fourth sidewall 48. Generally, the first sidewall 42 can be opposite and substantially identical to the third sidewall 46, while the second sidewall 44 can be opposite and substantially identical to the fourth sidewall 48.

In one example, with reference to FIGS. 6-8, the second sidewall 44 and the fourth sidewall 48 can be substantially smooth or planar. The first sidewall 42 and third sidewall 46 can each include a limiting projection or lip 50 and a channel 52. The lip 50 can be formed adjacent to the receiver surface 22a. Each lip 50 can extend along the respective one of the first sidewall 42 and third sidewall 46 from the second sidewall 44 to the fourth sidewall 48. Generally, each lip 50 can extend outwardly from the respective one of the first sidewall 42 and third sidewall 46. A size of a width of the lip 50 can be used to control or limit the range of uniplanar motion of the bone fastener 14.

Figure 4:
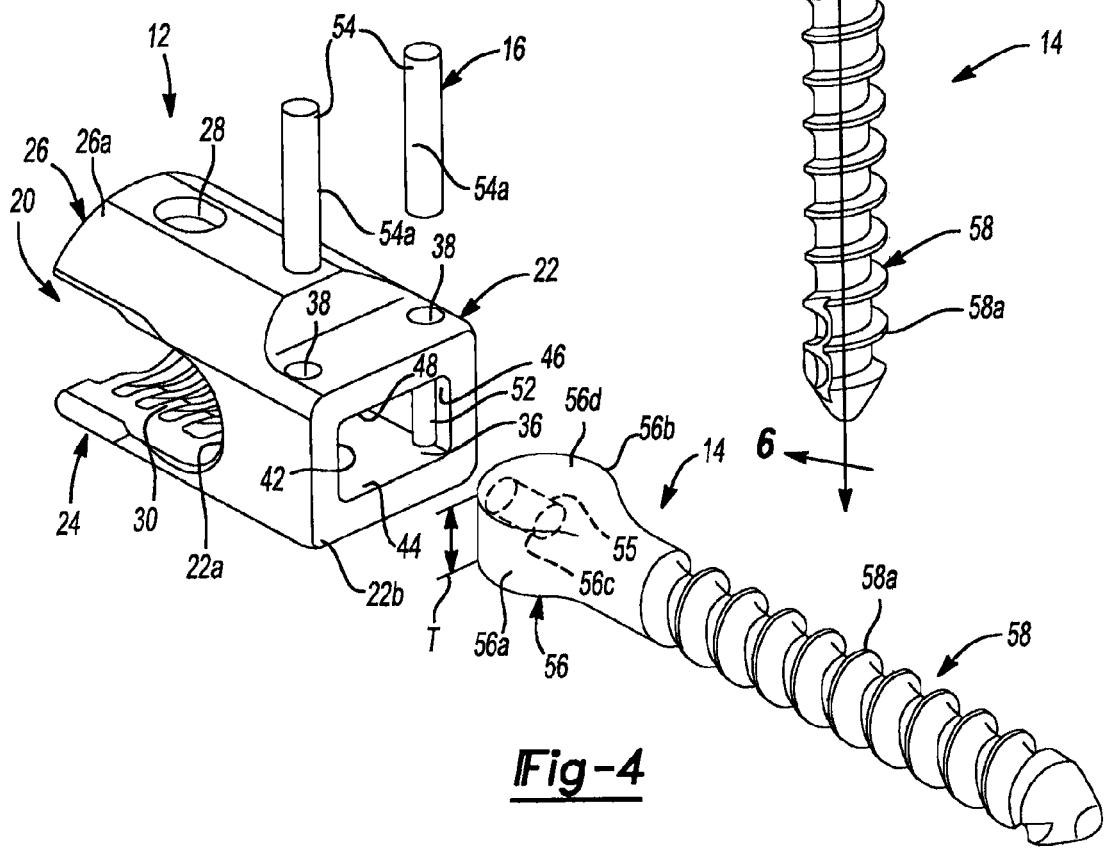
FIG. 4 is an exploded view of the uniplanar bone anchor system of FIG. 1.
Figure 5:
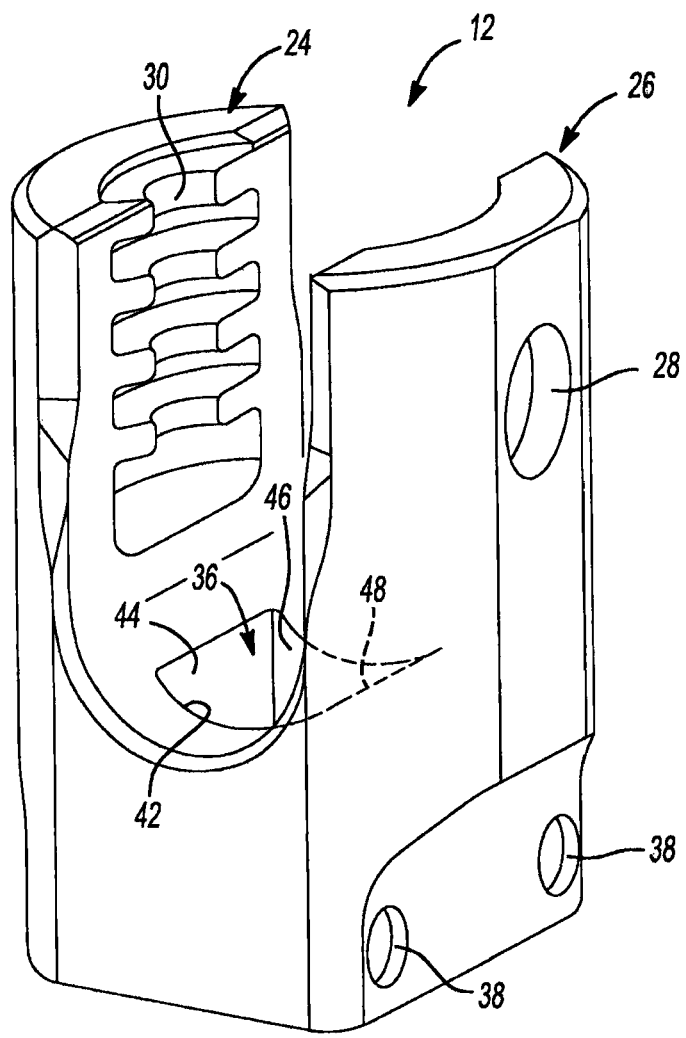
FIG. 5 is a perspective view of an exemplary saddle for use with the uniplanar bone anchor system of FIG. 1.

The channel 52 can be formed adjacent to or near the bottom surface 22b. Each channel 52 can be in communication with a respective one of the coupling bores 38, and can define a passageway for receipt of a portion of the coupling system 16, as will be discussed. Each channel 52 can be defined along the respective one of the first sidewall 42 and third sidewall 46 from the second sidewall 44 to the fourth sidewall 48. Each channel 52 can be substantially cylindrical, and in one example, each channel 52 can be circumferentially open along a length of the channel 52 that extends from the second sidewall 44 to the fourth sidewall 48 (FIG. 4). Generally, the channel 52 can be circumferentially open to enable the coupling system 16 to contact a portion of the bone fastener 14, as will be discussed.

The coupling bores 38 can be sized to receive the coupling system 16 therein. In one example, the coupling bores 38 can be annular, and can be formed adjacent to the bottom surface 22b of the distal end 22. The coupling bores 38 can be defined through the second sidewall 44 and the fourth sidewall 48. Generally, the coupling system 16 can be press-fit into the coupling bores 38, however, any suitable technique could be used to couple the coupling system 16 to the distal end 22 of the saddle 12, such as adhesives, welding, etc. Thus, the coupling bores 38 can have any desired shape to mate with the coupling system 16, such as square, keyed, etc. The coupling bores 38 can cooperate with the coupling system 16 to enable the bone fastener 14 to move in only one plane, as will be discussed further herein.

The bone fastener 14 can be received through the central bore 36 of the saddle 12, and can be coupled to the saddle 12 via the coupling system 16. With reference to FIGS. 4 and 6-8, the bone fastener 14 can include a proximal end or head 56 and a distal end or shaft 58. The head 56 can be configured to retain the bone fastener 14 within the saddle 12, and can be coupled to the connecting rod 18. In one example, the head 56 can be an annular ring, and can have a thickness T. The thickness T can be sized to ensure that the head 56 can move in a single plane. Optionally, the head 56 can also include a bore 55, which can be configured to enable the bone fastener 14 to be coupled to a respective vertebral body V. In one example, the bore 55 can be threaded, to matingly engage a plurality of threads on a suitable tool, such as a drill. If employed, the bore 55 can cooperate with the tool to align the shaft 58 axially during the insertion of the bone fastener 14 into the anatomy.

The head 56 can define a first bearing surface 56a, a second bearing surface 56b, a first planar surface 56c and a second planar surface 56d. The first bearing surface 56a can be generally opposite the second bearing surface 56b, and the first planar surface 56c can be generally opposite the second planar surface 56d. The first bearing surface 56a and the second bearing surface 56b can be adjacent to the first sidewall 42 and the third sidewall 46 when the bone fastener 14 is positioned within the saddle 12. Similarly, the first planar surface 56c and the second planar surface 56d can be adjacent to the second sidewall 44 and the fourth sidewall 48 when the bone fastener 14 is positioned within the saddle 12.

The first bearing surface 56a and the second bearing surface 56b can be in communication with a portion of the coupling system 16 so that the bone fastener 14 can articulate relative to the saddle 12 in one plane. The first planar surface 56c and the second planar surface 56d can cooperate with the second sidewall 44 and the fourth sidewall 48 to restrict or prevent the motion of the bone fastener 14 in more than one plane, as will be discussed herein.

The shaft 58 can be configured to engage the anatomy to secure the bone fastener 14 to the anatomy. In one example, the shaft 58 can include a plurality of threads 58a, which can couple the bone fastener 14 to a desired vertebral body V. It should be noted that the shaft 58 may include other or additional generally known features to facilitate the coupling of the bone fastener 14 to the anatomy, such as flutes, grooves, etc.

With reference to FIGS. 4 and 6-8, in one example, the coupling system 16 can comprise at least one or more pins 54. The pins 54 can be composed of any suitable biocompatible material, such as a biocompatible metal, metal alloy or polymer. The pins 54 can have a length, which can enable the pins 54 to extend through the second sidewall 44 and the fourth sidewall 48, along the first sidewall 42 and third sidewall 46. The pins 54 can be generally cylindrical, and can each include a bearing surface 54a. A respective one of the bearing surfaces 54a can contact the first bearing surface 56a, while the other of the bearing surfaces 54a can contact the second bearing surface 56b of the bone fastener 14 to enable the bone fastener 14 to articulate relative to the coupling system 16. In addition, the contact between the pins 54 and the bone fastener 14 can retain the bone fastener 14 within the saddle 12.

Figure 9:
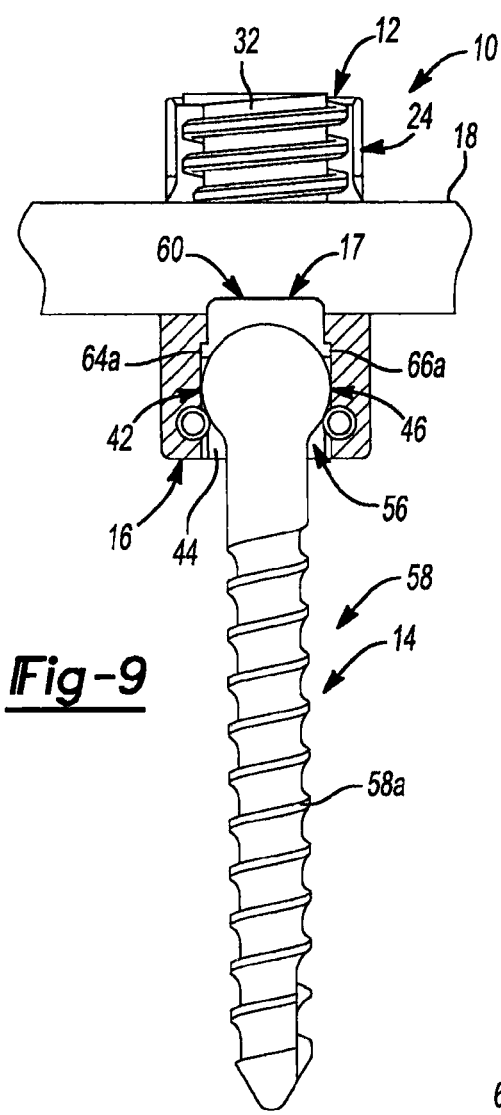
FIG. 9 is a schematic cross-sectional illustration of another exemplary uniplanar bone anchor system for use with a connecting device in a fixation procedure according to the present teachings.
Figure 10:
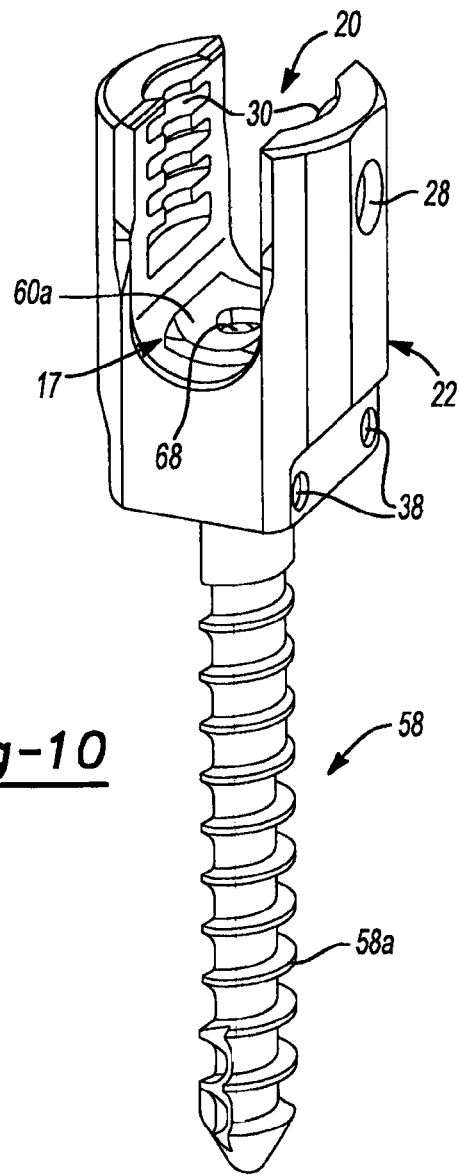
FIG. 10 is a perspective view of the uniplanar bone anchor system of FIG. 9.
Figure 11:
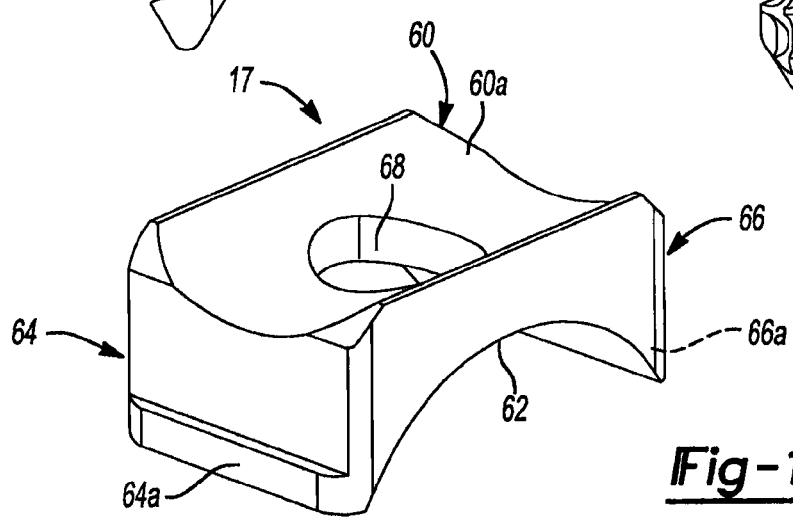
FIG. 11 is a perspective view of an exemplary pressure cap for use with the uniplanar bone anchor system of FIG. 9.

With brief reference to FIGS. 9-11, the pressure cap 17 can be optionally coupled to the head 56 of the bone fastener 14 to further distribute forces across the head 56 of the bone fastener 14. It should be noted that the pressure cap 17 is optional, as the contact between the bone fastener 14 and the connecting rod 18 alone can distribute forces across the head 56 of the bone fastener 14 (FIG. 9). The pressure cap 17 can generally be sized to be positioned within the central bore 36 of the saddle 12.

In one example, the pressure cap 17 can be sized such that a first or top surface 60 of the pressure cap 17 extends slightly above the receiver surfaces 22a of the saddle 12 when the pressure cap 17 is coupled to the saddle 12 (FIG. 10). This can allow the pressure cap 17 to apply a force to the head 56 of the bone fastener 14 when the connecting rod 18 is coupled to the saddle 12 via the set screw 32 (FIG. 9). This force applied by the pressure cap 17 can provide for more controlled movement of the bone fastener 14 due to the frictional forces acting between the pressure cap 17 and the bone fastener 14. In addition, the use of the pressure cap 17 with the bone fastener 14 provides a larger surface area for the distribution of forces acting on the bone fastener 14. It should be noted, however, that the pressure cap 17 could also be sized to enable the pressure cap 17 to be press-fit into the central bore 36 of the saddle 12 to apply the force to the bone fastener 14, if desired. With reference to FIG. 11, the pressure cap 17 can include the top surface 60 opposite a second or bottom surface 62, a first sidewall 64 opposite a second sidewall 66 and a central bore or aperture 68.

The top surface 60 can define an arcuate or concave groove 60a, which can extend from the first sidewall 64 to the second sidewall 66. The groove 60a can generally be sized to receive a portion of the connecting rod 18, such that a portion of the connecting rod 18 can be supported by the top surface 60. The bottom surface 62 can be arcuate or concave, and generally, can be shaped to mate with the head 56 of the bone fastener 14. The bottom surface 62 can be smooth to enable the bone fastener 14 to move relative to the pressure cap 17.

The first sidewall 64 and the second sidewall 66 can each extend from the top surface 60 to the bottom surface 62. The first sidewall 64 and the second sidewall 66 can each include a lip or projection 64a, 66a, respectively. With reference to FIG. 9, the projections 64a, 66a can be configured to extend below or under the lips 50 of the first sidewall 42 and third sidewall 46 of the central bore 36. The projections 64a, 66a can cooperate with the lips 50 to retain the pressure cap 17 within the central bore 36 of the saddle 12 against the force of gravity when the saddle 12 is rotated.

The aperture 68 can be defined about a central axis of the pressure cap 17. The aperture 68 can have a diameter, which can be sized to enable a suitable tool to pass through the pressure cap 17 to facilitate coupling the bone fastener 14 to the anatomy. In one example, the diameter of the aperture 68 can be about as large as or larger than a diameter of the bore 55 formed in the head 56 of the bone fastener 14. It should be noted, however, that in the case of a press-fit pressure cap 17, an aperture 68 need not be provided as the bone fastener 14 could be coupled to the anatomy prior to pressing the pressure cap 17 into the saddle 12.

With reference to FIGS. 2 and 9, the connecting rod 18 can be coupled to or retained within the saddle 12. The connecting rod 18 can be coupled to the saddle 12 via a suitable mechanical fastener, such as the set screw 32. An exemplary connecting rod 18 and set screw 32 can be substantially similar to the connecting rod and set screw employed in the Polaris™ 5.5 Spinal System, commercially available from Biomet, Inc. of Warsaw, Ind., or the connecting element disclosed in commonly owned U.S. Patent Publication No. 2008/0077138, filed on Apr. 20, 2007 and previously incorporated by reference herein. As the connecting rod 18 and the set screw 32 can be generally known, the connecting rod 18 and set screw 32 need not be discussed in great detail herein.

Briefly, however, the connecting rod 18 can comprise an elongated solid cylindrical tube or solid shaft. The connecting rod 18 can also include a slight curvature, which can correspond to the natural curvature of the spine. Typically, the connecting rod 18 can be composed of a suitable biocompatible material having sufficient rigidity to fix the vertebral bodies V relative to each other. The set screw 32 can include threads, which can matingly engage the threads formed on the mating portion 30 of the proximal end 20 of the saddle 12.

The ability of the bone fastener 14 to move in one plane relative to the saddle 12 can allow the saddle 12 to move in one plane when the bone fastener 14 is fixedly coupled to the anatomy. In turn, this can allow the surgeon to position the saddle 12 in a desired position relative to the bone fastener 14 prior to coupling the connecting rod 18 to the saddle 12 with the set screw 32. As the surgeon tightens the set screw 32 onto the connecting rod 18, the connecting rod 18 can be pushed onto the head 56 of the bone fastener 14 or the pressure cap 17, which can secure or fix the bone fastener 14 in the desired position relative to the saddle 12. By allowing the surgeon to select a desired position for the saddle 12 relative to the bone fastener 14, the surgeon can more easily insert the connecting rod 18 into the saddles 12. In addition, the positioning of the saddles 12 prior to the coupling of the connecting rod 18 can allow for a better alignment of the patient's spine.

With reference to FIG. 9, in order to assemble the bone anchor system 10, the pressure cap 17, if employed, can be positioned in the central bore 36 of the saddle 12 such that the projections 64a, 66a are in contact with the lips 50. Then, the bone fastener 14 can be positioned through the central bore 36 of the saddle 12. Next, with reference to FIGS. 6-8, the pins 54 of the coupling system 16 can be inserted or pressed through the coupling bores 38, into the channels 52 of the first sidewall 42 and third sidewall 46 of the central bore 36. Once the coupling system 16 is pressed into the saddle 12, the bone fastener 14 can be retained in the saddle 12 such that the bone fastener 14 is movable in only one plane.

In this regard, the third planar surface 56c and fourth planar surface 56d of the bone fastener 14 can be in contact with the smooth or planar second sidewall 44 and fourth sidewall 48 of the central bore 36, thereby restricting or limiting the motion of the bone fastener 14 to a single plane, as shown in FIGS. 6-8. The single plane of motion can be defined by the bearing surfaces 54a of the pins 54 and the projections 64a, 66a of the pressure cap 17 or at least one of the lips 50 of the first sidewall 42 and third sidewall 46 if the pressure cap 17 is not employed.

In one example, the bearing surfaces 54a of the pins 54 can contact the first bearing surface 56a and the second bearing surface 56b of the bone fastener 14 to enable the bone fastener 14 to articulate relative to the coupling system 16. The lips 50 of the central bore 36 or the projections 64a, 66a of the pressure cap 17 can limit the articulation of the bone fastener 14 relative to the coupling system 16. As the bone fastener 14 moves or articulates in the single plane, a portion of the first bearing surface 56a and the second bearing surface 56b of the bone fastener 14 can contact at least one of the lips 50 of the saddle 12, thereby preventing further movement or articulation of the bone fastener 14 (FIGS. 6 and 8). Thus, the saddle 12 and the coupling system 16 can restrict or limit the motion of the bone fastener 14 to a single plane.

In this regard, the bone fastener 14 can require about three points of contact to allow the motion of the bone fastener 14 to be a single plane. In one example, the head 56 of the bone fastener 14 can require about three points or lines of contact to form a substantially circular path or single substantially circular plane about which the bone fastener 14 can rotate. For example, the head 56 can contact each of the pins 54 and one of the lips 50; one of the pins 54 and both of the lips 50; one of the pins 54, one of the lips 50 and one of the second or fourth sidewalls 44, 48 of the central bore 36, etc.

With the bone fastener 14 coupled to the saddle 12 via the coupling system 16, surgical access can be made through the skin adjacent to the vertebral bodies V of interest (FIG. 1). The specific surgical access approaches are beyond the scope of the present application, but for example, surgical access can be obtained via a minimally invasive surgical procedure such as that used with the Polaris™ 5.5 Spinal System, commercially available from Biomet, Inc. of Warsaw, Ind., or the minimally invasive surgical procedure disclosed in commonly owned U.S. Patent Publication No. 2008/0077138, filed on Apr. 20, 2007 and previously incorporated by reference herein.

Next, one or more bone anchor systems 10 can be coupled to a respective vertebral body V via the bone fastener 14. Various techniques can be used to couple the bone anchor systems 10 to the anatomy, such as those described in commonly owned U.S. Patent Publication No. 2008/0077138, filed on Apr. 20, 2007, previously incorporated by reference herein. In one example, if each bone fastener 14 includes the bore 55 defined in the head 56, a suitable tool can be coupled to the bore 55 to align and drive the bone fastener 14 into the anatomy in a conventional manner. Once the bone anchor systems 10 are coupled to the anatomy, the saddles 12 can be moved into a desired position relative to the bone fastener 14 by the surgeon. Then, the connecting rod 18 can be inserted into the saddle 12 of each of the bone anchor systems 10. Generally, the connecting rod 18 can be inserted such that the connecting rod 18 rests on the head 56 of the bone fastener 14 (FIG. 2) and optionally, a portion of the groove 60a of the pressure cap 17 (FIG. 9).

With the connecting rod 18 positioned in the saddles 12 of the bone anchor systems 10, the set screw 32 can be coupled to each mating portion 30 of each saddle 12 (FIGS. 2 and 9). The coupling of the set screw 32 can apply a force to the pressure cap 17 to move the groove 60a of the pressure cap 17 substantially adjacent to the receiver surfaces 22a of the saddle 12, if employed. This movement of the pressure cap 17 can apply a force to the head 56 of the bone fastener 14, which can distribute forces over the head 56 of the bone fastener 14. The coupling of the set screw 32 to the saddle 12 can couple the connecting rod 18 to the bone anchor system 10.

As discussed, since the surgeon is able to position the saddles 12 relative to the bone fasteners 14 prior to coupling the connecting rod 18 to the respective bone anchor system 10, the surgeon can more easily insert the connecting rod 18 into the saddles 12. In addition, the positioning of the saddles 12 prior to the coupling of the connecting rod 18 can allow for a better alignment of the patient's spine.

With reference now to FIGS. 12-15, in one example, a bone anchor system 100 can be employed with the connecting rod 18 to repair a damaged portion of an anatomy. As the bone anchor system 100 can be similar to the bone anchor system 10 described with reference to FIGS. 1-11, only the differences between the bone anchor system 10 and the bone anchor system 100 will be discussed in great detail herein, and the same reference numerals will be used to denote the same or similar components. The bone anchor system 100 can include a saddle 102, the bone fastener 14 and a uniplanar coupling system 106. It should be noted that although not illustrated herein, the bone anchor system 100 can include the pressure cap 17, if desired.

With reference to FIGS. 12-15, the saddle 102 can be substantially U-shaped and symmetrical with respect to a longitudinal axis L defined by the bone anchor system 100 (FIG. 14). The saddle 102 can include the proximal end 20 and a second or distal end 110. The distal end 110 can be generally rectangular, and can include the receiver surface 22a and a bottom surface 110b. It should be noted, however, that the distal end 110 can have any desired shape, such as circular, octagonal, etc. The distal end 110 can also include a central aperture or central bore 112 and at least one coupling apertures or coupling bore 114. The central bore 112 can be defined through the distal end 22 from the receiver surface 22a to the bottom surface 110b. Generally, the central bore 112 can be sized to receive the bone fastener 14, and can cooperate with the coupling system 106 to allow the bone fastener 14 to move in only one plane. The central bore 112 can include the first sidewall 42, the second sidewall 44, a third sidewall 116 and the fourth sidewall 48. Generally, the first sidewall 42 can be opposite, but not identical to the third sidewall 116.

In one example, the third sidewall 116 can include the limiting lip 50 and a tapered portion 116a. The tapered portion 116a can be defined in the third sidewall 116 adjacent to the bottom surface 110b to provide relief for the uniplanar motion of the bone fastener 14. Thus, the tapered portion 116a can cooperate with the coupling system 106 to enable the bone fastener 14 to move further in only one plane. Generally, the tapered portion 116a can be sized to permit angular motion of the bone fastener 14 in the single plane. For example, the tapered portion 116a can have a slope of about negative 30 degrees to about negative 60 degrees relative to the longitudinal axis L. The slope of the tapered portion 116a along with the lip 50 can define an angular limit for the motion of the bone fastener 14 relative to the third sidewall 116 of the saddle 12.

Figure 12:
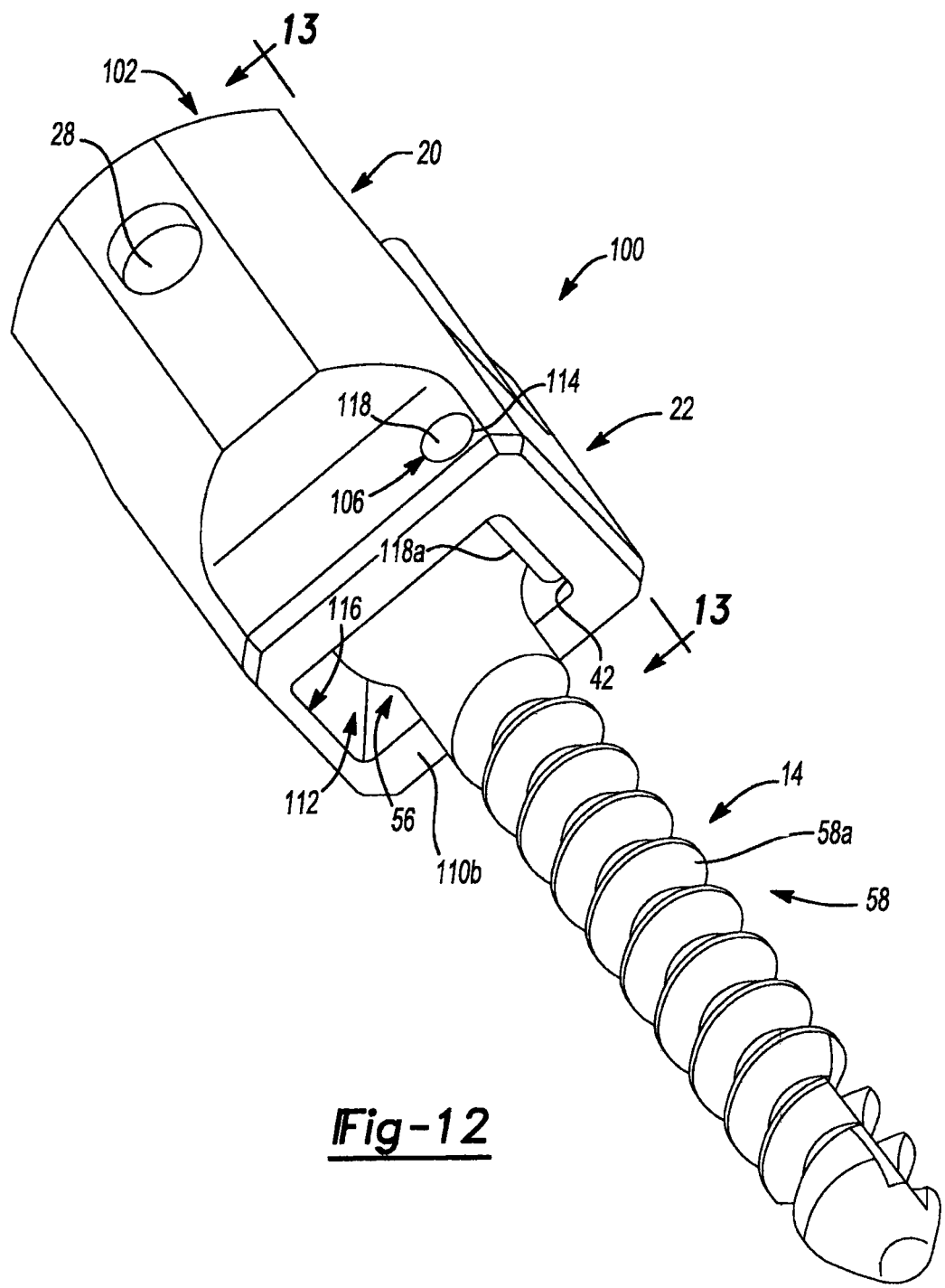
FIG. 12 is a schematic perspective illustration of another exemplary uniplanar bone anchor system for use with a connecting device in a fixation procedure according to the present teachings.
Figure 16:
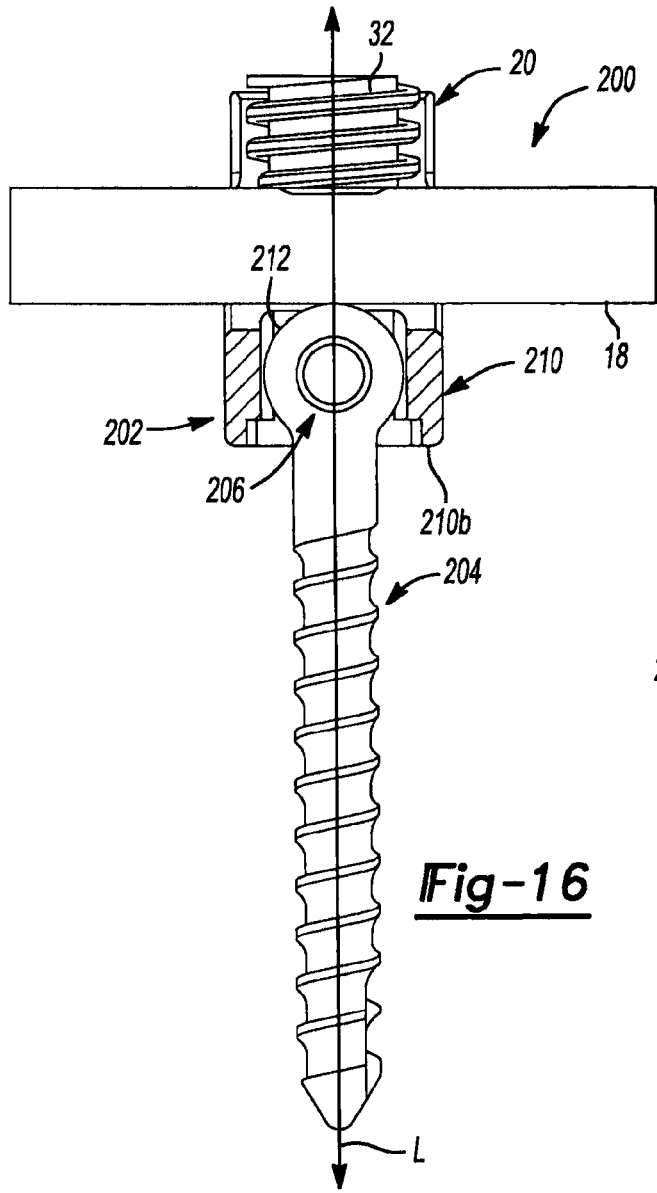
FIG. 16 is a schematic partial cross-sectional illustration of another exemplary uniplanar bone anchor system for use with a connecting device in a fixation procedure according to the present teachings.
Figure 17:
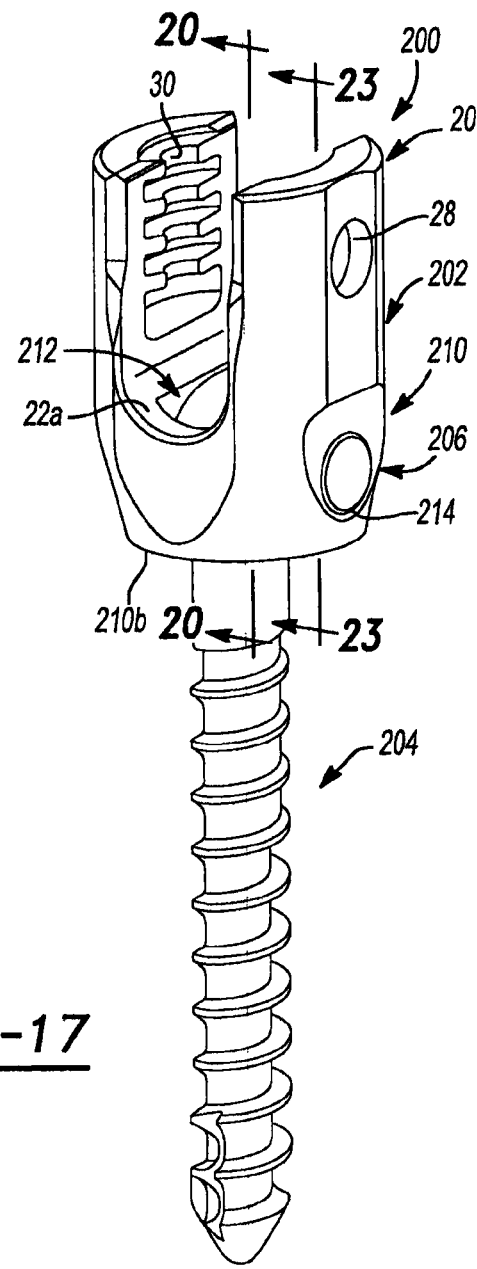
FIG. 17 is a schematic perspective illustration of the uniplanar bone anchor system of FIG. 16.

With reference to FIG. 12, the at least one coupling bore 114 can comprise a single coupling bore 114 defined through the first sidewall 42. As the coupling bore 114 can be substantially similar to one of the coupling bores 38 discussed with regard to FIGS. 1-11, the coupling bore 114 need not be discussed in great detail herein. Briefly, however, the coupling bore 114 can cooperate with the coupling system 106 to enable the bone fastener 14 to move in only one plane.

With reference to FIGS. 12-15, the coupling system 106 can comprise at least one pin 118, and in this example, the coupling system 106 can include a single pin 118. As the pin 118 can be substantially similar to one of the pins 54 discussed with regard to FIGS. 1-11, the pin 118 need not be discussed in great detail herein. Briefly, however, the pin 118 can include a bearing surface 118a. The pin 118 can be received within the channel 52 such that the bearing surface 118a can contact the first bearing surface 56a of the bone fastener 14 to enable the bone fastener 14 to move in only one plane.

In order to assemble the bone anchor system 100, the pressure cap 17, if employed, can be positioned in the central bore 36 of the saddle 102 such that the projections 64a, 66a are in contact with the lips 50. Then, the bone fastener 14 can be positioned through the central bore 36 of the saddle 102. Next, the pin 118 of the coupling system 106 can be inserted or pressed through the coupling bore 114, into the channel 52 of the first sidewall 42 of the saddle 102. Once the coupling system 106 is pressed into the saddle 102, the bone fastener 14 can be retained in the saddle 102 such that the bone fastener 14 is movable in only one plane.

In this regard, with reference to FIGS. 13-15, the third planar surface 56c and fourth planar surface 56d of the bone fastener 14 can be in contact with the smooth or planar second sidewall 44 and fourth sidewall 48 of the central bore 36, thereby defining the motion of the bone fastener 14 as a single plane. The single plane of motion can be defined by the bearing surface 118a of the pin 118, the non-tapered portion of the third sidewall 116 and the lips 50 of the first sidewall 42 and third sidewall 116.

In one example, the bearing surface 118a of the pin 118 can contact the first bearing surface 56a (FIG. 13), while the non-tapered portion of the third sidewall 116 can contact the second bearing surface 56b of the bone fastener 14 to enable the bone fastener 14 to articulate relative to the coupling system 106 (FIG. 15).

As the surgical insertion and use of the bone anchor system 100 in a fixation procedure can be similar to the surgical insertion and insertion of the bone anchor system 10 in a fixation procedure, the surgical insertion and use of the bone anchor system 100 need not be discussed in great detail herein.

With reference now to FIGS. 16-24, in one example, a bone anchor system 200 can be employed with the connecting rod 18 to repair a damaged portion of an anatomy. As the bone anchor system 200 can be similar to the bone anchor system 10 described with reference to FIGS. 1-11, only the differences between the bone anchor system 10 and the bone anchor system 200 will be discussed in great detail herein, and the same reference numerals will be used to denote the same or similar components. The bone anchor system 200 can include a saddle 202, a bone fastener 204 and a uniplanar coupling system 206. The bone anchor system 200 can also include the pressure cap 17, if desired.

With reference to FIGS. 16-19, the saddle 202 can be substantially U-shaped and symmetrical with respect to a longitudinal axis L defined by the bone anchor system 200. The saddle 202 can include the proximal end 20 and a second or distal end 210. The distal end 210 can be generally rectangular, and can include the receiver surface 22a and a bottom surface 210b. The distal end 210 can also include a central aperture or central bore 212 and at least one coupling aperture or coupling bore 214.

In one example, the central bore 212 can be formed along the longitudinal axis L from the receiver surface 22a to the bottom surface 210b. Generally, the central bore 212 can be sized to receive the bone fastener 204, and can cooperate with the coupling system 206 to allow the bone fastener 204 to move in only one plane. With reference to FIGS. 19-23, the central bore 212 can include a first sidewall 216, a second sidewall 218, a third sidewall 220 and a fourth sidewall 222. The first sidewall 216 can be opposite and substantially identical to the third sidewall 220, while the second sidewall 218 can be opposite and substantially identical to the fourth sidewall 222.

Figure 24:
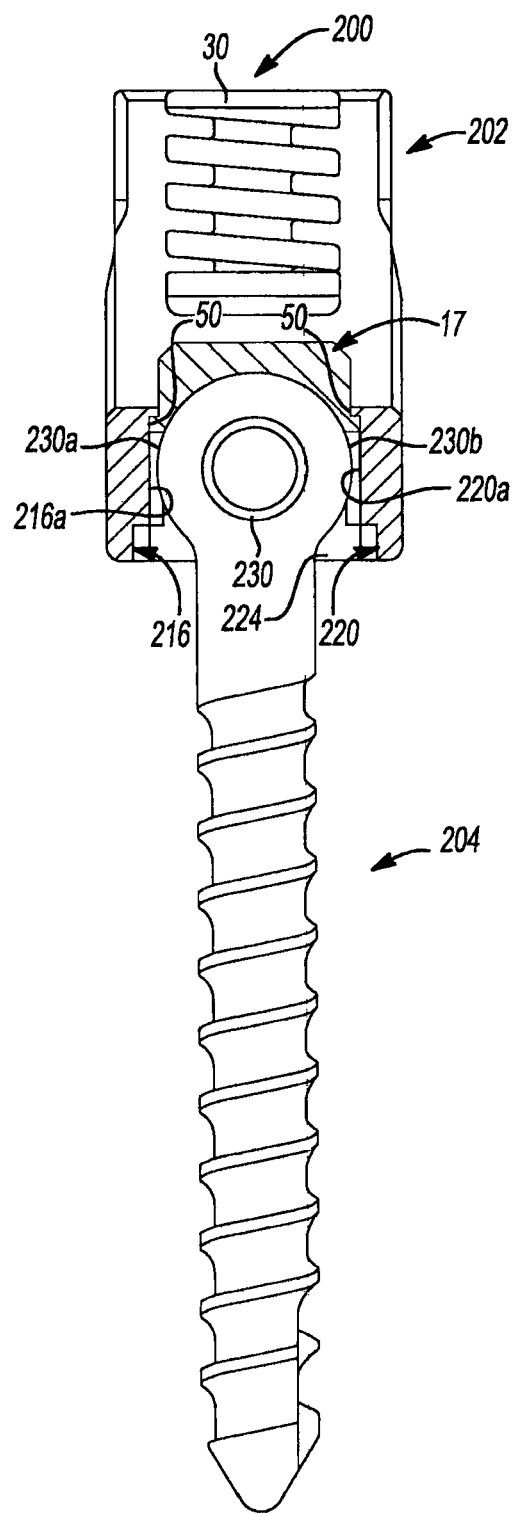
FIG. 24 is a schematic cross-sectional illustration of another exemplary uniplanar bone anchor system, similar to the uniplanar bone anchor system of FIGS. 16-23, for use with a connecting device in a fixation procedure according to the present teachings.

With reference to FIG. 24, in one example, the first sidewall 216 and third sidewall 220 can each include the lip 50, if desired, which can be used to couple the pressure cap 17 to the saddle 202. The first sidewall 216 and third sidewall 220 can also include a counter bore 224 formed adjacent to the bottom surface 22b. The counter bore 224 can be defined from the second sidewall 218 to the fourth sidewall 222. The counter bore 224 can provide a contact or stop for the movement of the bone fastener 204 relative to the saddle 202.

Figure 23:
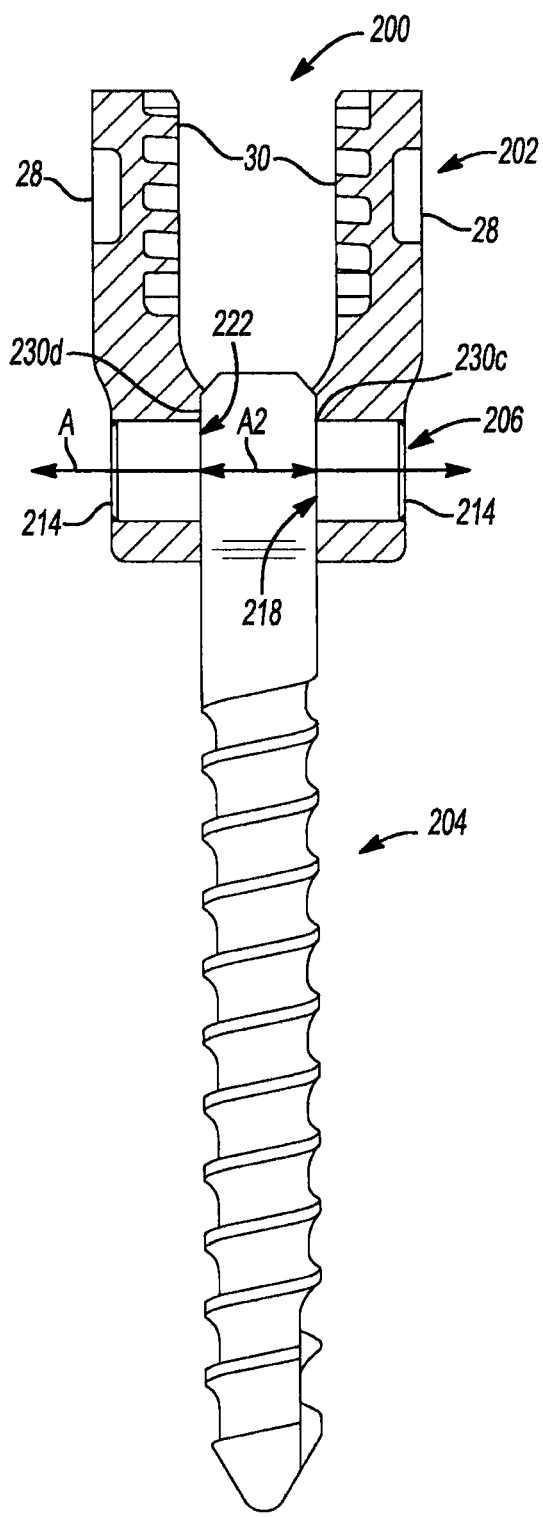
FIG. 23 is a schematic, cross-sectional illustration of the uniplanar bone anchor system, taken along line 23-23 of FIG. 17.

In one example, with reference to FIGS. 18-24, the coupling bore 214 can be defined through the second sidewall 218 and the fourth sidewall 222. Thus, the coupling bore 214 can be formed transverse to the longitudinal axis L of the bone anchor system 200. With reference to FIG. 23, the coupling bore 214 can have an axis A, which can be substantially perpendicular to the longitudinal axis L. The coupling bore 214 can have any shape configured to receive the coupling system 206, and for example, the coupling bore 214 can be annular. It should be noted, however, the coupling bore 214 could have any desired shape, such as rectangular, square, etc. The coupling bore 214 can receive the coupling system 206 to couple the bone fastener 204 to the saddle 202 such that the bone fastener 204 is confined to only one plane of motion, as will be discussed in further detail herein.

With reference to FIG. 18, the bone fastener 204 can include a proximal end or head 230 and the shaft 58. The head 230 can be configured to retain the bone fastener 204 within the saddle 202. In one example, the head 230 can be annular, and can have a thickness T. The thickness T can be sized so that the head 230 can be retained within the central bore 212. Optionally, the head 230 can include the bore 55, which can be configured to enable the bone fastener 204 to be coupled to a respective vertebral body V. The head 230 can define a first surface 230a, a second surface 230b, a first planar surface 230c, a second planar surface 230d and a bore 230e.

The first surface 230a can be generally opposite the second surface 230b. The first bearing surface 230a and the second bearing surface 230b can be configured to articulate with the bearing surfaces 216a, 220a of the first sidewall 216 and the third sidewall 220, respectively, when the bone fastener 204 is positioned within the saddle 202. In one example, the first surface 230a and the second surface 230b can be generally arcuate, concave surfaces that can rotate relative to the first sidewall 216 and third sidewall 220 (FIGS. 20-22). The first surface 230a and the second surface 230b can cooperate with the second sidewall 218, and the fourth sidewall 222 or the coupling system 206 to enable the bone fastener 204 to move in only one plane, as will be discussed in greater detail herein.

With reference to FIG. 23, the first planar surface 230c can be generally opposite the second planar surface 230d. The first planar surface 230c and the second planar surface 230d can be adjacent to and substantially in contact with the second sidewall 218 and the fourth sidewall 222 when the bone fastener 204 is positioned within the saddle 202. The first planar surface 230c and the second planar surface 230d can cooperate with the second sidewall 218 and the fourth sidewall 222 to prevent the motion of the bone fastener 204 relative to the second sidewall 218 and the fourth sidewall 222. Thus, the first planar surface 230c and the second planar surface 230d and the second sidewall 218 and the fourth sidewall 222 can define or limit the motion of the bone fastener 204 to a single plane.

The bore 230e can be defined through the first planar surface 230c and the second planar surface 230d of the bone fastener 204. The bore 230e can generally be configured to be in communication with at least a portion of the coupling system 206, and thus, the bore 230e can have any suitable shape, such as rectangular, square, triangular, etc. In one example, with reference to FIG. 23, the bore 230e can be generally annular, and can have an axis A2, which can be parallel to the axis A of the coupling bore 214. The bore 230e can receive at least a portion of the coupling system 206 to couple the bone fastener 204 to the saddle 202 such that the bone fastener 204 can move in only one plane.

In this regard, with reference to FIG. 18, the coupling system 206 can comprise a pin 236, which can be received through the coupling bore 214 of the saddle 202 and the bore 230e of the bone fastener 204. The pin 236 can be composed of any suitable biocompatible material, such as a biocompatible metal, metal alloy or polymer. The pin 236 can couple the bone fastener 204 to the saddle 202, while defining a pivot axis for the movement of the bone fastener 204, as shown in FIGS. 20-22. In this regard, the bone fastener 204 can rotate about the pin 236 or the bone fastener 204 and pin 236 can rotate about the axis A in only one plane perpendicular to the axis A.

In order to assemble the bone anchor system 200, the pressure cap 17, if employed, can be positioned in the central bore 212 of the saddle 202 such that the projections 64a, 66a are in contact with the first lips 50 (FIG. 24). Then, the bone fastener 204 can be positioned through the central bore 212 of the saddle 202. Next, the pin 236 of the coupling system 206 can be inserted or pressed through the coupling bore 214 of the saddle 102 and the bore 230e of the bone fastener 204. Once the coupling system 206 is pressed into the saddle 102 through the bone fastener 204, the bone fastener 204 can be retained in the saddle 202 such that the bone fastener 204 is movable in only one plane.

In this regard, with reference to FIG. 23, the third planar surface 56c and fourth planar surface 56d of the bone fastener 14 can be in contact with the smooth or planar second sidewall 218 and fourth sidewall 222 of the central bore 212, thereby defining or limiting the motion of the bone fastener 204 to a single plane. As shown in FIGS. 20-22, the single plane of motion can be defined by the pin 236. The pin 236 can enable the bone fastener 204 to move between the counter bore 224 of the first sidewall 216 and third sidewall 220.

In other words, during the movement of the bone fastener 204, the first surface 230a and the second surface 230b can contact the first sidewall 216 and third sidewall 220, and the bone fastener 204 can articulate relative to the first sidewall 216 and third sidewall 220 about the pin 236 (FIGS. 20 and 22). The counter bore 224 of the central bore 212 can limit the articulation of the bone fastener 204 relative to the coupling system 206. Thus, the saddle 202 and the coupling system 206 can define or limit the motion of the bone fastener 204 to a single plane.

As the surgical insertion and use of the bone anchor system 200 in a fixation procedure can be similar to the surgical insertion and insertion of the bone anchor system 10 in a fixation procedure, the surgical insertion and use of the bone anchor system 200 need not be discussed in great detail herein.

With reference now to FIGS. 25-30, in one example, a bone anchor system 300 can be employed with the connecting rod 18 to repair a damaged portion of an anatomy. As the bone anchor system 300 can be similar to the bone anchor system 10 described with reference to FIGS. 25-30, only the differences between the bone anchor system 10 and the bone anchor system 300 will be discussed in great detail herein, and the same reference numerals will be used to denote the same or similar components. The bone anchor system 300 can include a saddle 302, a bone fastener 304 and a uniplanar coupling system 306.

Figure 27:
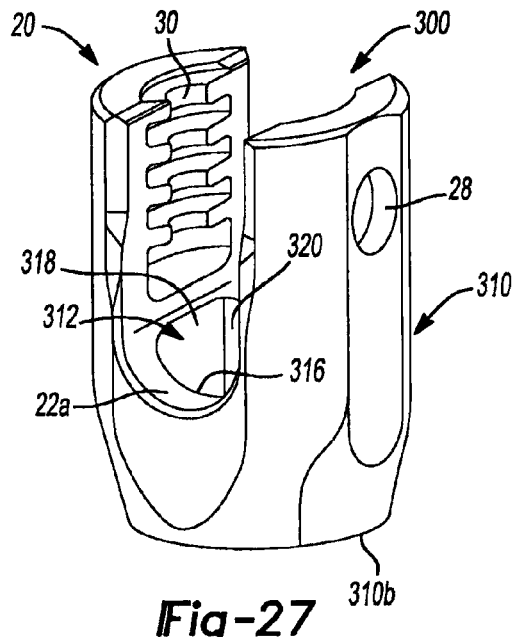
FIG. 27 is a perspective view of an exemplary saddle for use with the uniplanar bone anchor system of FIG. 25.

With reference to FIGS. 25-27, the saddle 302 can be substantially U-shaped and symmetrical with respect to a longitudinal axis L defined by the bone anchor system 300. The saddle 302 can include the proximal end 20 and a second or distal end 310. The distal end 310 can be generally conical and can include a slight taper. It should be noted, however, that the distal end 310 can have any desired shape, such as rectangular, circular, octagonal, etc. The distal end 310 can include the receiver surface 22a and a bottom surface 310b. The distal end 310 can also include a central aperture or central bore 312, which can extend from the receiver surface 22a to the bottom surface 310b. The central bore 312 can be spherical and sized to receive the bone fastener 304, and can cooperate with the coupling system 306 to allow the bone fastener 304 to move in only one plane.

Figure 30:
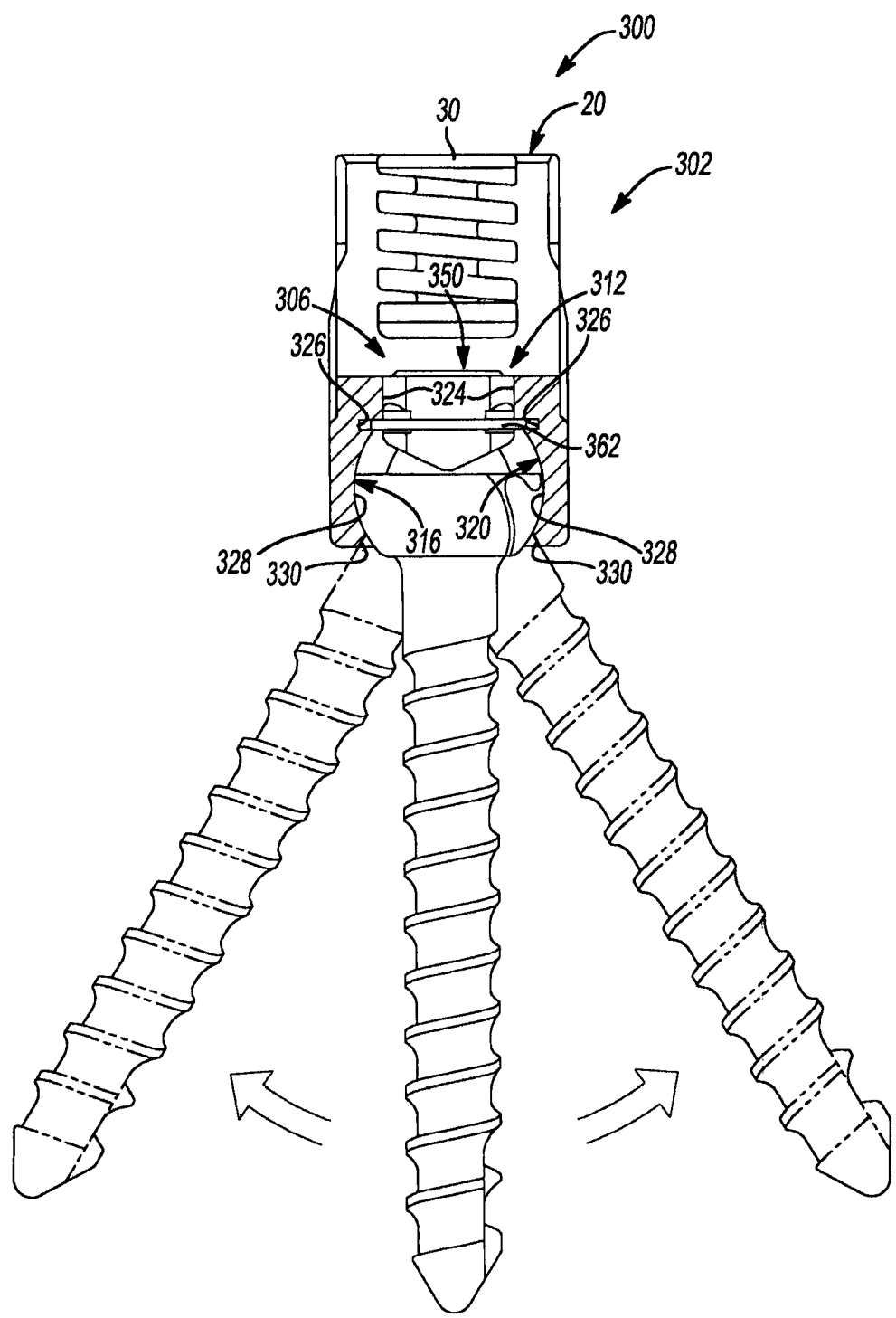
FIG. 30 is a schematic, cross-sectional illustration of the uniplanar bone anchor system, taken along line 30-30 of FIG. 25, which illustrates a range of uniplanar motion for the uniplanar bone anchor system.

With reference to FIGS. 27 and 30, the central bore 312 can include a first sidewall 316, a second sidewall 318, a third sidewall 320 and a fourth sidewall 322. The first sidewall 316 can be opposite the third sidewall 320, while the second sidewall 318 can be opposite the fourth sidewall 322. In one example, the first sidewall 316, the second sidewall 318, the third sidewall 320 and the fourth sidewall 322 can be substantially identical. With reference to FIG. 30, each of the first sidewall 316, the second sidewall 318, the third sidewall 320 and the fourth sidewall 322 can include a planar portion 324, a slot 326, an arcuate portion 328 and a tapered portion 330. Generally, the arcuate portion 328 can comprise a continuous sphere.

The planar portion 324 can be formed adjacent to the receiver surface 22a. Each of the planar portions 324 of the first sidewall 316, the second sidewall 318, the third sidewall 320 and the fourth sidewall 322 can cooperate to form a substantially rectangular portion. In addition, the planar portion 324 can cooperate with a portion of the coupling system 306 to limit the motion of the bone fastener 304 to only one plane, as will be discussed.

The slot 326 can be defined in the planar portion 324 of each of the first sidewall 316, the second sidewall 318, the third sidewall 320 and the fourth sidewall 322. In one example, the slot 326 can be formed adjacent to the arcuate portion 328. It should be noted, however, that the slot 326 can be formed in the arcuate portion 328, if desired. The slot 326 can be sized to receive a portion of the coupling system 306, and can couple a portion of the coupling system 306 to the saddle 302, as will be discussed.

The arcuate portion 328 can have a radius of curvature, which can extend from the slot 326 to the tapered portion 330. The arcuate portion 328 can generally comprise a concave surface formed in each of the first sidewall 316, the second sidewall 318, the third sidewall 320 and the fourth sidewall 322. Thus, the arcuate portion 328 can form a substantially spherical portion of the central bore 312. The arcuate portion 328 can receive a portion of the coupling system 306, and can cooperate with the coupling system 306 to define or limit the motion of the bone fastener 304 to a single plane.

The tapered portion 330 can be formed adjacent to the distal end 22 of the saddle 302. The tapered portion 330 can define an area of reduced thickness in the distal end 310 of the saddle 302, which can provide clearance to enable the bone fastener 304 to move in the single plane relative to the saddle 302.

With reference to FIG. 26, the bone fastener 304 can include a proximal end or head 340 and the shaft 58. In one example, the head 340 can include a projection 342, the bore 55 and a groove 344. The projection 342 can be a hemispherical ring, and can extend from a surface S of the head 340. The projection 342 can have a width WP, which can be selected to enable the bone fastener 304 to be coupled to a portion of the coupling system 306. As will be discussed, the projection 342 can define a bearing surface 342a, which can enable the bone fastener 304 to move relative to the saddle 302 via the receiver surface 356. Two planar surfaces 342b can be formed on opposite sides and can be generally perpendicular to the bearing surface 342a, to cooperate with the coupling system 306 to prevent the motion of the bone fastener 304 in more than one plane. The projection 342 can also define a peak or apex, through which the bore 55 can be defined.

The groove 344 can be defined below the surface S of the head 340, and can extend about a circumference of the head 340. The groove 344 can be configured to receive a portion of the coupling system 306 to couple the coupling system 306 to the bone fastener 304. It should be noted, however, that any suitable mechanism could be employed to couple the portion of the coupling system 306 to the bone fastener 304, such as mechanical fasteners, snap-fit, adhesives, etc.

Figure 28:
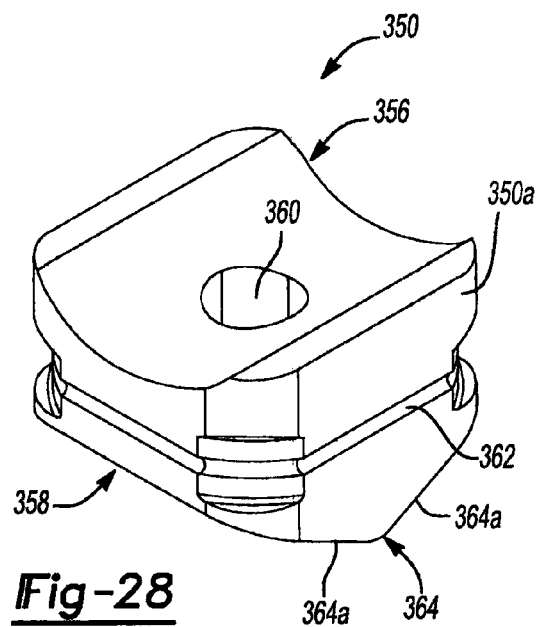
FIG. 28 is a perspective view of an exemplary cap for use with the uniplanar bone anchor system of FIG. 25.

With continued reference to FIG. 26, the coupling system 306 can comprise a cap 350, a support ring 352 and at least one support 354. The cap 350 can be substantially symmetrical about the longitudinal axis L. The cap 350 can be shaped and sized to be positioned within the rectangular portion of the central bore 312 defined by the planar portions 324, as shown in FIG. 30. The cap 350 can be composed of any suitable biocompatible material, such as a biocompatible metal, metal alloy and/or polymer. With reference to FIGS. 26 and 28, the cap 350 can include a top or receiver surface 356, a bottom surface 358, central bore or aperture 360 and a groove 362.

Figure 28A:
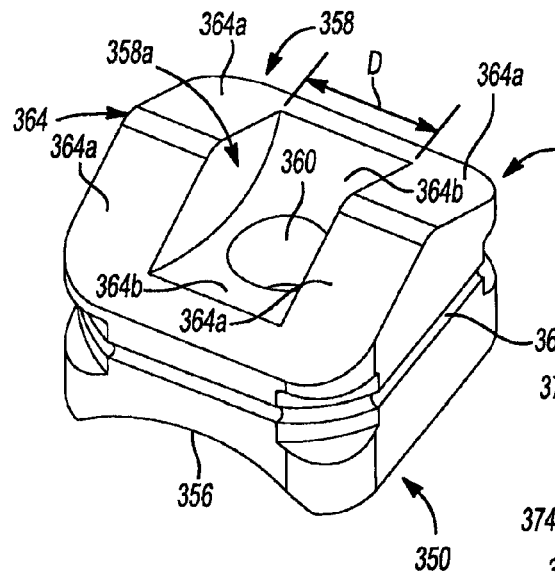
FIG. 28A is a perspective view of a bottom surface of the cap of FIG. 28.

The receiver surface 356 of the cap 350 can receive a portion of the connecting rod 18, and can be substantially similar in shape to the receiver surface 22a of the saddle 302. With reference to FIG. 28A, the bottom surface 358 can be opposite the receiver surface 356, and can include at least one protrusion 364. In one example, the bottom surface 358 can include two protrusions 364, which can be spaced apart by a distance D. The distance D can be substantially equal to the width WP of the projection 342 of the head 340 of the bone fastener 304 so that the projection 342 can be received between the two protrusions 364. The portion of the bottom surface 358 between the two protrusions 364 can comprise a bearing surface 358a, which can mate with the bearing surface 342a of the head 340 to enable the bone fastener 304 to articulate relative to the coupling system 306.

Each of the protrusions 364 can be triangular in shape, and can include at least one edge 364a and an interior planar surface 364b. In the case of a triangular shaped protrusion 364, each protrusion 364 can include two edges 364a. Each of the edges 364a can serve as a stop or limit for the motion of the bone fastener 304 in the single plane. In this regard, each of the edges 364a can contact a portion of the at least one support 354, thereby limiting further movement of the bone fastener 304. The interior planar surfaces 364b of the protrusions 364 can be adjacent to the planar surfaces 342b of the head 340 of the bone fastener 304 to limit the motion of the bone fastener 304 to a single plane. In other words, the contact between the interior planar surfaces 364b of the cap 350 and the planar surfaces 342b of the head 340 can prevent the movement of the bone fastener 304 in the direction of either interior planar surface 364b. Thus, the cap 350 can limit the motion of the bone fastener 304 to only one plane, as will be discussed further herein.

The aperture 360 can be defined through the receiver surface 356 and the bottom surface 358. The aperture 360 can enable a suitable tool to pass through the cap 350 and engage the bore 55 to couple the bone fastener 304 to the anatomy. The groove 362 can extend outwardly from the cap 350, and can be formed about an outer surface 350a of the cap 350. The groove 362 can be sized to cooperate with the slot 326 of the saddle 302 to couple the cap 350 to the saddle 302 (FIG. 30). In one example, the groove 362 can be configured such that support ring 352 can snap into engagement with the slot 326. It should be noted, however, that any suitable coupling technique could be used to secure the cap 350 to the saddle 302, such as a flange, press fit, etc.

With reference back to FIG. 26, the coupling system 306 can include the support ring 352. The supporting ring 352 can be configured to be received within the groove 344 of the head 340 (FIG. 30). In one example, the supporting ring 352 can be snap-fit into the groove 344 and groove 362, however, the support ring 352 can be coupled to the groove 344 and groove 362 in any desired manner. Further, the support ring 352 could be integrally formed with the at least one support 354, if desired. The support ring 352 can couple the at least one support 354 to the bone fastener 304.

Figure 29:
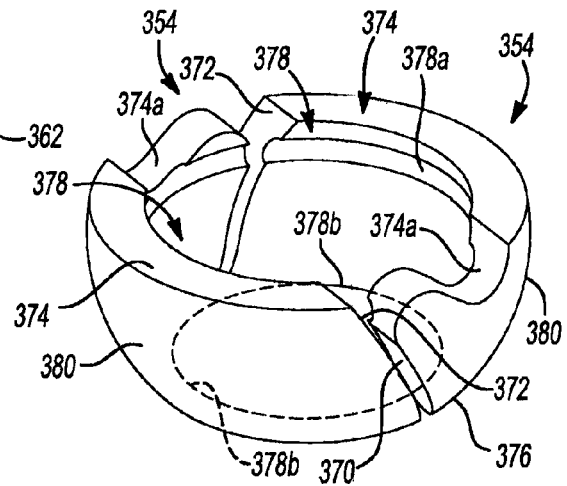
FIG. 29 is a perspective view of an exemplary support for use with the uniplanar bone anchor system of FIG. 25.

The at least one support 354 can retain the bone fastener 304 within the saddle 302. In one example, the at least one support 354 can comprise two supports 354, which together can surround the circumference of the head 340 of the bone fastener 304 (FIG. 30). It should be noted, however, that more or less supports 354 (e.g. one) could be employed to retain the head 340 of the bone fastener 304 within the saddle 302, if desired. The supports 354 can be received within the spherical portion of the central aperture 312 defined by the arcuate portions 328 when the bone anchor system 300 is assembled (FIG. 30). With reference to FIG. 29, the supports 354 can each include a first end 370, a second end 372, a first or proximal side 374, a second or distal side 376, an interior surface 378 and an exterior surface 380.

The first end 370 and second end 372 can each be angled or sloped relative to the longitudinal axis L of the bone anchor system 300. The sloped nature of the first end 370 and second end 372 can facilitate the placement of the supports 354 relative to each other. The proximal side 374 can be adjacent to the head 340 of the bone fastener 304, while the distal side 376 can be adjacent to the shaft 58 of the bone fastener 304. The proximal side 374 can have a larger radius of curvature than the radius of curvature of the distal side 376 as the supports 354 can be configured to mate with the head 340 and shaft 58 of the bone fastener 304. The proximal side 374 can include a notch 374a, which can allow a suitable instrument to engage the support 354 for coupling and uncoupling the support 354 from the bone fastener 304.

The interior surface 378 can include a channel 378a and a collar 378b. The channel 378a can be formed adjacent to the proximal side 374. The channel 378a can extend for a substantial majority of the interior surface 378 and can be sized to mate with the support ring 352 to couple the support 354 to the bone fastener 304. The collar 378b can be formed adjacent the distal side 376, and can also extend for a substantial majority of the interior surface 378. The collar 378b can be configured to mate with a portion of the shaft 58 of the bone fastener 304 when the support 354 is coupled to the support ring 352. The exterior surface 380 of the support 354 can be generally smooth to contact the spherical portion of the central bore 312.

With reference to FIGS. 26 and 30, in order to assemble the bone anchor system 300, the support ring 352 can be coupled to the groove 344 of the bone fastener 304. Then, the bone fastener 304 can be coupled to the saddle 302. In this regard, the bone fastener 304 can be advanced into the central bore 312 from the distal end 310 of the saddle 302 until the projection 342 of the bone fastener 304 is positioned between the protrusions 364 of the cap 350. Next, the supports 354 can be coupled to the bone fastener 304 via the engagement of the channel 378a with the support ring 352. The cap 350 can be positioned within the central bore 312 of the saddle 302, such that the cap 350 is in contact with the rectangular portion of the central bore 312 (FIG. 30). Once the cap 350 is coupled to the saddle 302, the movement of the bone fastener 304 is defined or limited to one plane, as shown in FIG. 30.

In this regard, the planar surfaces 342b of the head 340 can cooperate with the interior planar surfaces 364b of the cap 350 to limit the motion of the bone fastener 304 in the direction of either interior planar surface 364b. Thus, the cap 350 and head 340 of the bone fastener 304 limit the bone fastener 304 to a single plane of motion. The bearing surface 342a of the head 340 can allow the head 340 to articulate on the bearing surface 358a of the cap 350. The relative movement between the bearing surface 342a of the bone fastener 304 and the bearing surface 358a of the cap 350 can be defined by the edges 364a, which can contact a respective one of the supports 354 to prevent additional angular movement of the bone fastener 304 in the single plane. Thus, the saddle 302 and the coupling system 306 can define or limit the motion of the bone fastener 304 to a single plane.

As the surgical insertion and use of the bone anchor system 300 in a fixation procedure can be similar to the surgical insertion and insertion of the bone anchor system 10 in a fixation procedure, the surgical insertion and use of the bone anchor system 300 need not be discussed in great detail herein.

With reference now to FIGS. 31-35, in one example, a bone anchor system 400 can be employed with the connecting rod 18 to repair a damaged portion of an anatomy. As the bone anchor system 400 can be similar to the bone anchor system 300 described with reference to FIGS. 25-30, only the differences between the bone anchor system 300 and the bone anchor system 400 will be discussed in great detail herein, and the same reference numerals will be used to denote the same or similar components. The bone anchor system 400 can include the saddle 302, a bone fastener 404 and a uniplanar coupling system 406.

Figure 32:
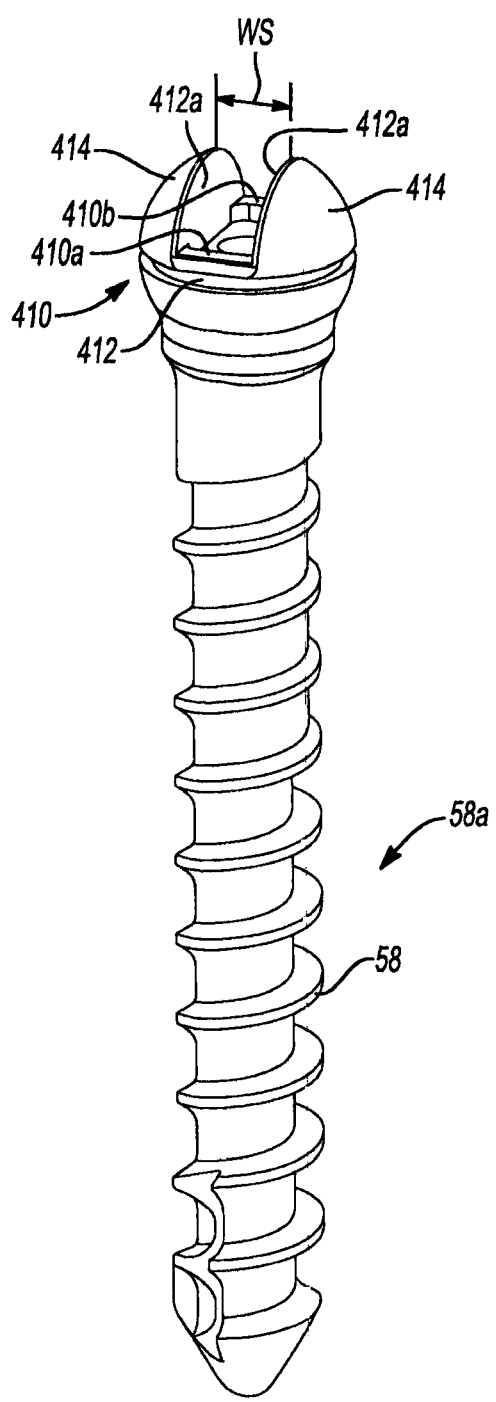
FIG. 32 is a perspective view of an exemplary bone fastener for use with the uniplanar bone anchor system of FIG. 31.

With reference to FIG. 32, the bone fastener 404 can include a proximal end or head 410 and the shaft 58. In one example, the head 410 can include a slot 412, at least one bearing surface 414, the bore 55 and the groove 344. The slot 412 can be defined through the head 410 from a first end 410a to a second end 410b. The slot 412 can include two parallel planar sidewalls 412a, which can be spaced apart by a distance D4. The slot 412 can receive a portion of the coupling system 406, and the sidewalls 412a can cooperate with the coupling system 406 to restrict or limit the motion of the bone fastener 404 to a single plane, as will be discussed herein. The at least one bearing surface 414, in this example, can comprise two bearing surfaces 414. The bearing surfaces 414 can each comprise hemispherical portions of the head 410 defined by the slot 412. The slot 412 can cooperate with the coupling system 406 to enable the bone fastener 404 to move in a single plane.

Figure 31:
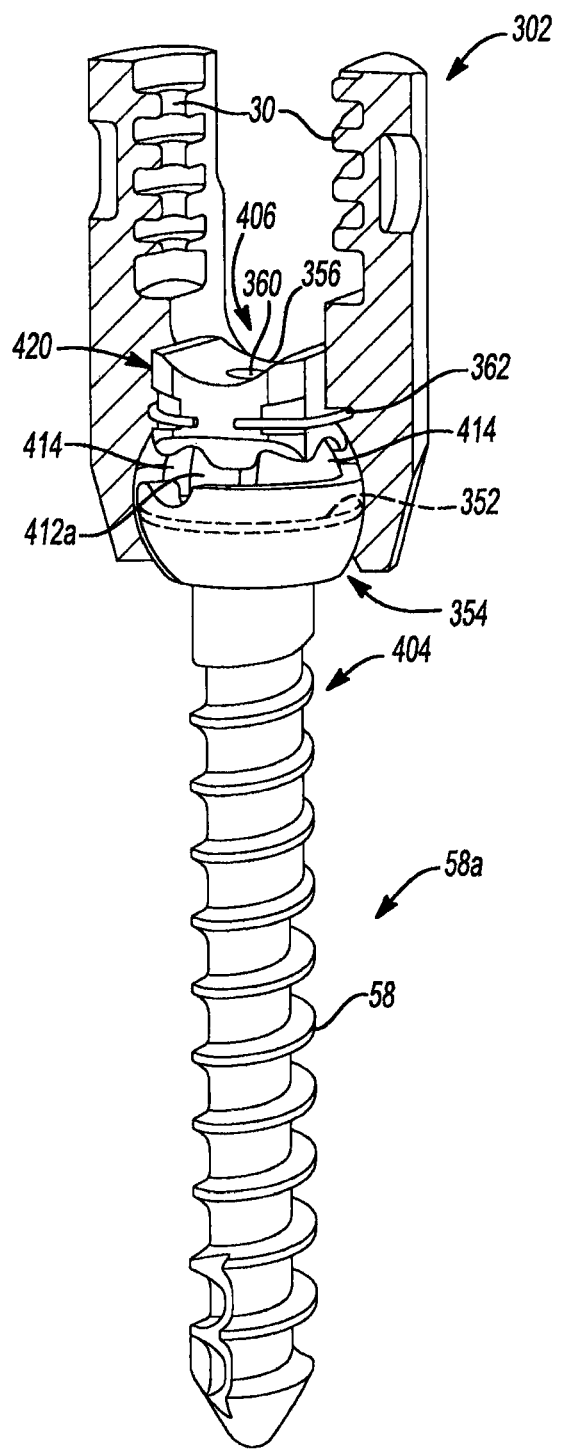
FIG. 31 is a schematic cross-sectional illustration of another exemplary uniplanar bone anchor system for use with a connecting device in a fixation procedure according to the present teachings.
Figure 33:
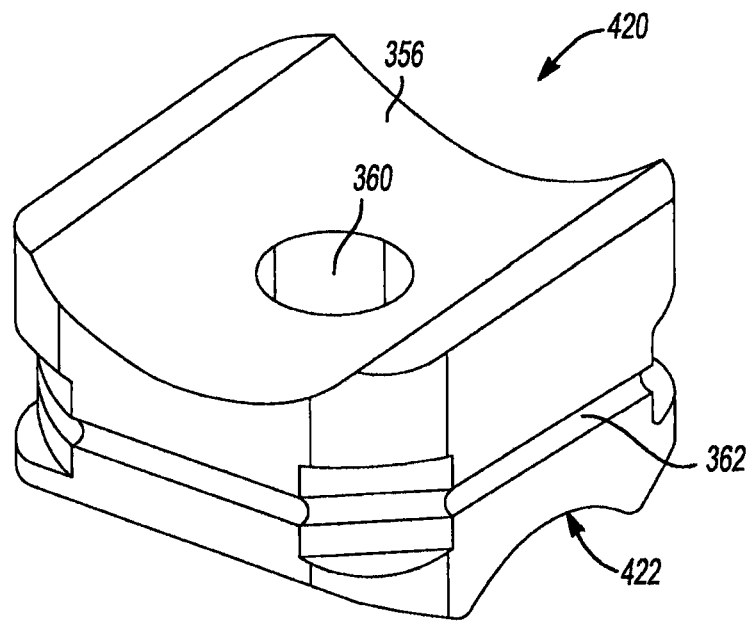
FIG. 33 is a perspective view of an exemplary cap for use with the uniplanar bone anchor system of FIG. 31.
Figure 34:
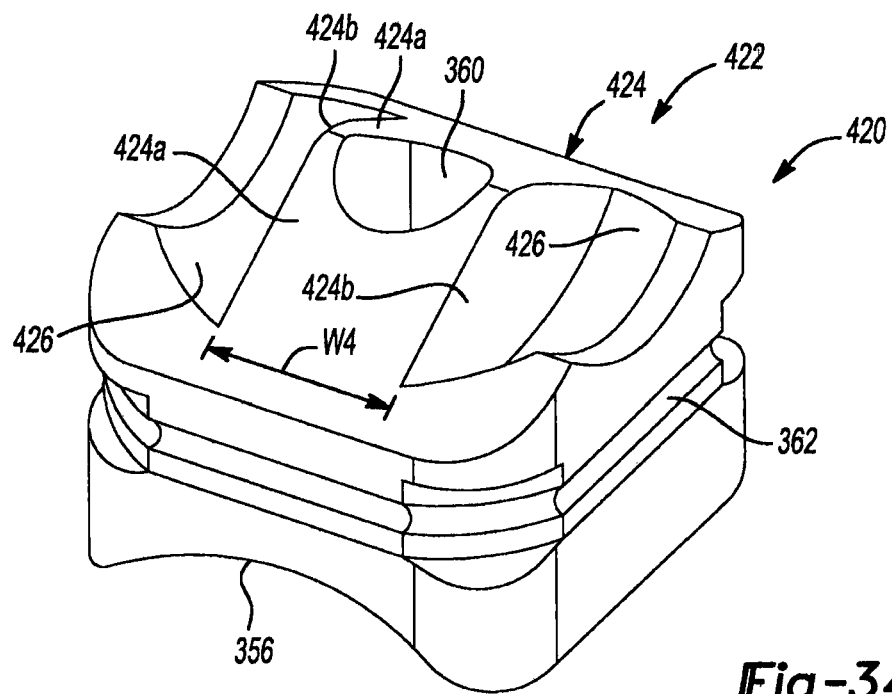
FIG. 34 is a perspective view of a bottom surface of the cap of FIG. 33.

With reference to FIG. 31, the coupling system 406 can comprise a cap 420, the support ring 352 and the at least one support 354. The cap 420 can be substantially symmetrical about the longitudinal axis L. The cap 420 can be shaped and sized to be positioned within the rectangular portion of the central bore 312 of the saddle 302. The cap 420 can be composed of any suitable biocompatible material, such as a biocompatible metal, metal alloy and/or polymer. With reference to FIGS. 33 and 34, the cap 420 can include the top or receiver surface 356, a bottom surface 422, the aperture 360 and the flange 362.

The bottom surface 422 can be opposite the receiver surface 356, and can include at least one protrusion 424 and at least one bearing surface 426. In one example, the protrusion 424 can be triangular in shape, and can extend outwardly from the bottom surface 422. The protrusion 424 can be sized to be received within the slot 412 of the head 410, and thus, can have a width W4, which can be substantially equal to a width W5 of the slot 412. The protrusion 424 can include at least one edge 424a and an interior planar surface 424b.

Figure 35:
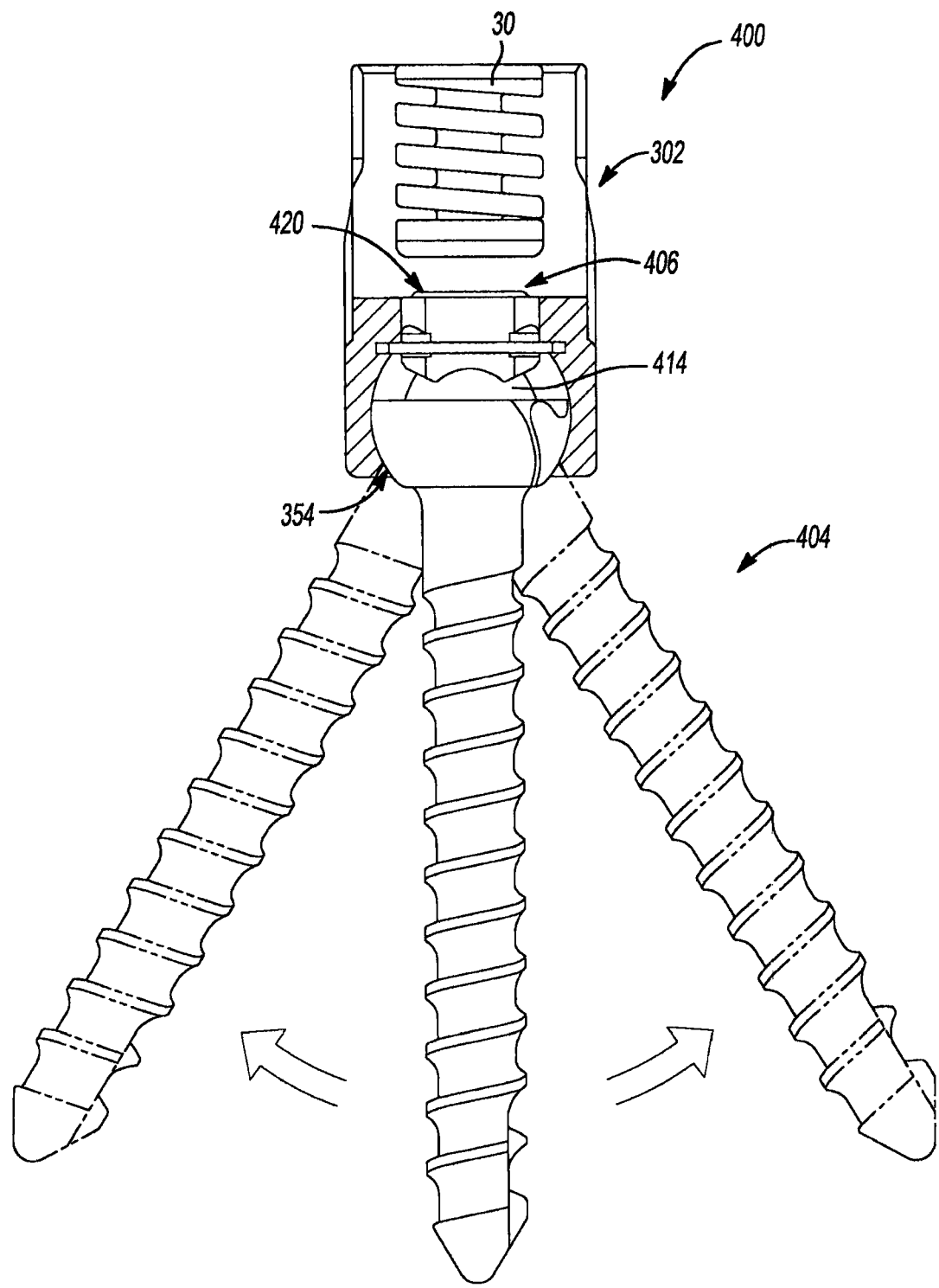
FIG. 35 is a schematic, cross-sectional illustration of the uniplanar bone anchor system, which illustrates a range of uniplanar motion for the uniplanar bone anchor system of FIG. 31.

In this example, the protrusion 424 can include two edges 424a. Each of the edges 424a can define the motion of the bone fastener 404 in the single plane. In this regard, each of the edges 424a can contact a portion of the slot 412, thereby limiting further movement of the bone fastener 404. The interior planar surfaces 424b of the protrusions 424 can be adjacent to the planar sidewalls 412a of the slot 412 of the bone fastener 404 to limit the motion of the bone fastener 404 to a single plane. In other words, the contact between the interior planar surfaces 424b of the cap 420 and the planar sidewalls 412a of the head 410 can prevent the movement of the bone fastener 404 in the direction of either planar sidewall 412a. Thus, the cap 420 can cooperate with the head 410 to define or limit the motion of the bone fastener 404 to only one plane, as shown in FIG. 35.

With reference now to FIG. 34, the at least one bearing surface 426 of the bottom surface 422, in this example, can comprise two bearing surfaces 426, which can be defined adjacent to each interior planar surface 424b. It should be noted, however, that the bottom surface 422 can include no bearing surfaces 426, if desired. The bearing surfaces 426 can cooperate with the bearing surfaces 414 of the head 410 to enable the bone fastener 404 to move or articulate relative to the saddle 302 in only one plane. In this example, the single plane of motion can be defined by the bearing surfaces 414 of the head 410 and the edges 424a of the cap 420. The relative movement between the bearing surfaces 414 of the bone fastener 404 and the bearing surfaces 426 of the cap 420 can be limited by the edges 424a, which can contact a portion of the slot 412 to prevent additional movement of the bone fastener 404 in the single plane, as illustrated in FIG. 35.

With reference to FIGS. 31-35, in order to assemble the bone anchor system 400, the support ring 352 can be coupled to the groove 344 of the bone fastener 404. Then, the bone fastener 404 can be coupled to the saddle 302. In this regard, the bone fastener 404 can be advanced into the central bore 312 from the distal end 310 of the saddle 302 until the protrusion 424 of the cap 420 is received by the slot 412 of the bone fastener 404. Next, the supports 354 can be coupled to the bone fastener 404 via the engagement of the channel 378a with the support ring 352. The cap 420 can be positioned within the central bore 312 of the saddle 302, such that the cap 420 is in contact with the rectangular portion of the central bore 312. Once the cap 420 is coupled to the saddle 302, the movement of the bone fastener 404 is restricted or limited to one plane, as discussed.

As the surgical insertion and use of the bone anchor system 400 in a fixation procedure can be similar to the surgical insertion and insertion of the bone anchor system 300 in a fixation procedure, the surgical insertion and use of the bone anchor system 400 need not be discussed in great detail herein.

With reference now to FIGS. 36-43, in one example, a bone anchor system 500 can be employed with the connecting rod 18 to repair a damaged portion of an anatomy. As the bone anchor system 500 can be similar to the bone anchor system 300 described with reference to FIGS. 25-30, only the differences between the bone anchor system 300 and the bone anchor system 500 will be discussed in great detail herein, and the same reference numerals will be used to denote the same or similar components. The bone anchor system 500 can include a saddle 502, the bone fastener 304 and a uniplanar coupling system 506.

Figure 38:
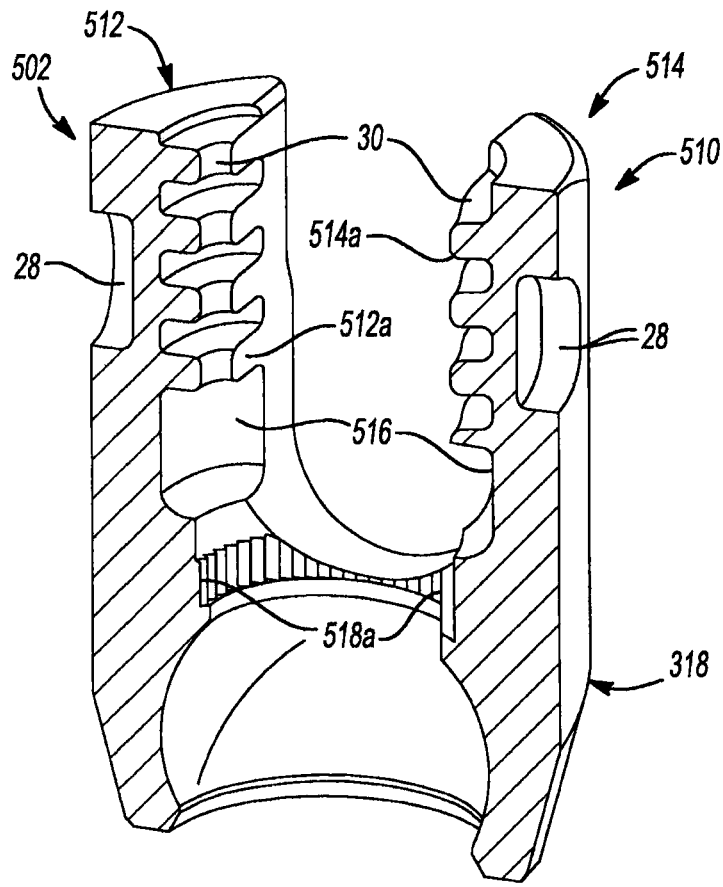
FIG. 38 is a perspective view of an exemplary saddle for use with the uniplanar bone anchor system of FIG. 36.

With reference to FIGS. 36-38, the saddle 502 can be substantially U-shaped and symmetrical with respect to a longitudinal axis L defined by the bone anchor system 500. The saddle 502 can include a first or proximal end 510 and the distal end 310. The proximal end 510 can include a first arm 512 and a second arm 514. The first arm 512 and second arm 514 can extend upwardly from the distal end 310 to define the U-shape. Each of the first arm 512 and the second arm 514 can include the insertion feature 28, the mating portion 30, a notch 516 and a locking portion 518. The mating portion 30 can be formed on an interior surface 512a, 514a, of each of the first arm 512 and second arm 514, respectively.

The notch 516 can be defined on the interior surfaces 512a, 514a of the first arm 512 and the second arm 514. In one example, the notch 516 can be formed between the mating portion 30 and the locking portion 518. The notch 516 can provide clearance for a portion of the coupling system 506, as will be discussed in greater detail herein.

The locking portion 518 can be formed between the proximal end 510 and the distal end 310. In one example, the locking portion 518 can be defined about a circumference of the proximal end 510, adjacent to or near the distal end 310. The locking portion 518 can include a plurality of teeth 518a, which can engage a portion of the coupling system 306 to prevent the rotation of a portion of the coupling system 306 relative to the saddle 502.

Figure 39:
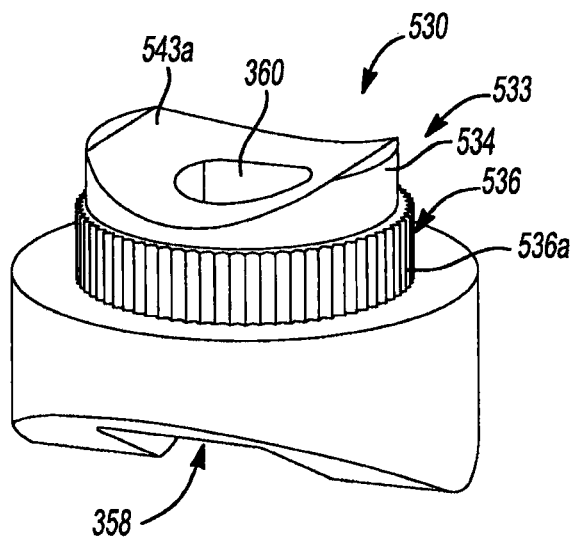
FIG. 39 is a perspective view of an exemplary cap for use with the uniplanar bone anchor system of FIG. 36.
Figure 40:
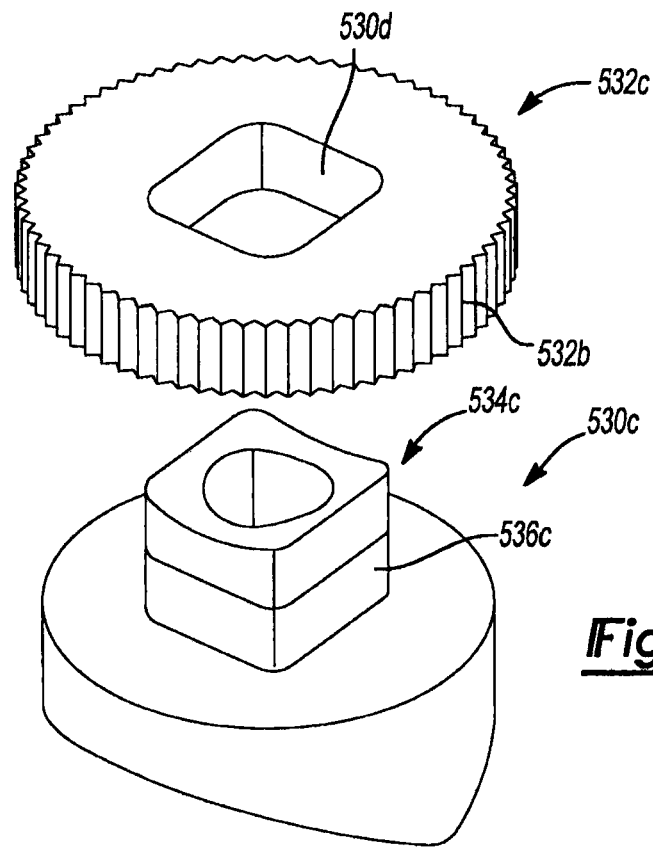
FIG. 40 is an exploded, perspective view of another exemplary locking member and cap for use with the uniplanar bone anchor system of FIG. 36.
Figure 42:
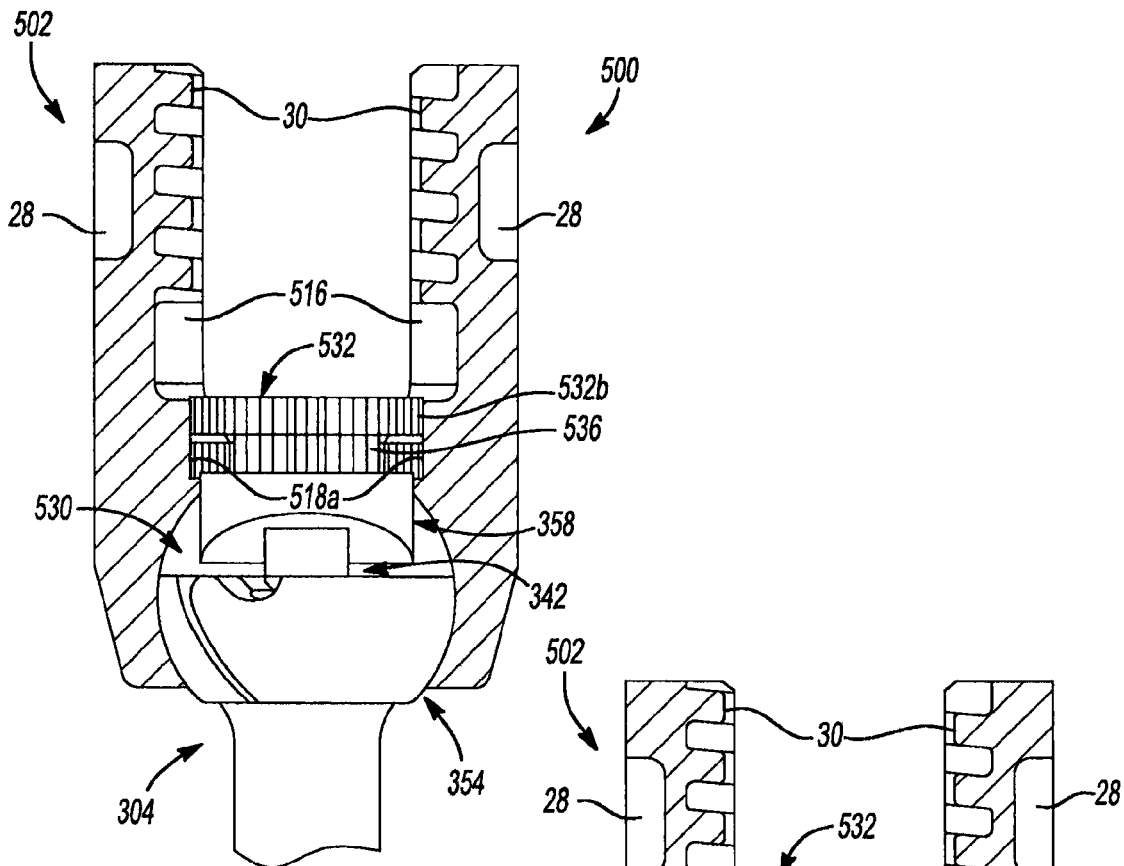
FIG. 42 is a schematic, cross-sectional illustration of the uniplanar bone anchor system of FIG. 36, which illustrates the locking member in a first, unlocked position to enable the selection of a desired single plane of motion.
Figure 43:
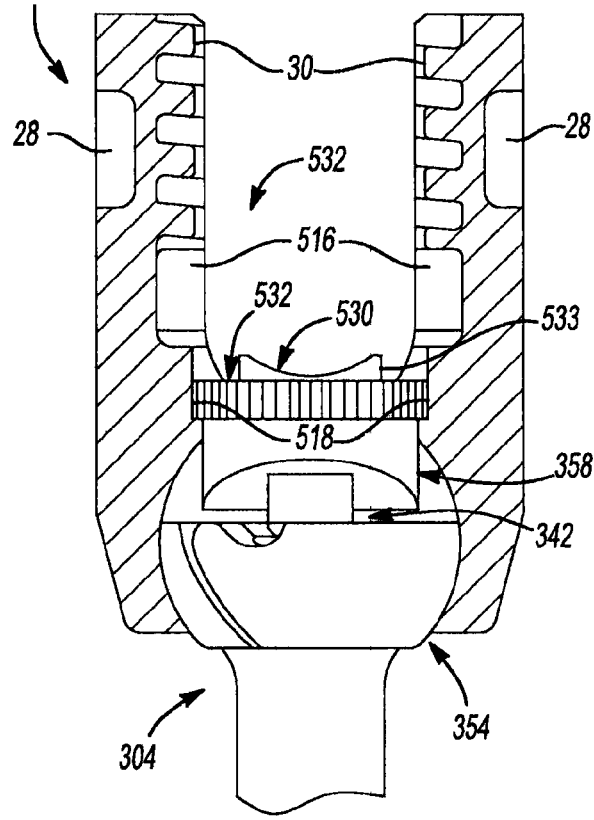
FIG. 43 is a schematic, cross-sectional illustration of the uniplanar bone anchor system of FIG. 36, which illustrates the locking member in a second, locked position.

With reference to FIGS. 37 and 39, the coupling system 406 can comprise a cap 530, a locking member 532, the support ring 352 and the supports 354. The cap 530 can be substantially symmetrical about the longitudinal axis L. The cap 530 can be shaped and sized to be positioned within the rectangular portion of the central bore 312 defined by the planar portions 324 (FIG. 42). The cap 530 can be composed of any suitable biocompatible material, such as a biocompatible metal, metal alloy and/or polymer. With reference to FIG. 39, the cap 530 can include a top surface 533, the bottom surface 358, and the aperture 360.

The top surface 533 can be opposite the bottom surface 358. The top surface 533 can include a projection 534 and a cap locking portion 536. The projection 534 can extend proximally from the cap 530. In one example, the projection 534 can be annular, however, the projection 534 could have any desired shape, such as square, rectangular, triangular, etc. The projection 534 can define a receiver surface 534a. The receiver surface 534a can be substantially similar in shape to the receiver surface 22a of the saddle 502. The aperture 360 can be defined from the receiver surface 534a to the bottom surface 358.

The cap locking portion 536 can be formed about a periphery of the projection 534. The cap locking portion 536 can include a plurality of teeth 536a. The teeth 536a can mate with a portion of the locking member 532 to prevent the rotation of the cap 530 relative to the saddle 502.

With reference to FIG. 37, the locking member 532 can comprise a ring, which can include a plurality of interior teeth 532a and a plurality of exterior teeth 532b. The interior teeth 532a can mate with the teeth 536a of the cap locking portion 536 to couple the locking member 532 to the cap 530. The interior teeth 532a can generally be formed about an inner circumference of the locking member 532, while the exterior teeth 532b can be formed about an outer circumference of the locking member 532. The exterior teeth 532b can mate with the teeth 518a of the locking portion 518 of the saddle 502 to prevent the rotation of the cap 530 relative to the saddle 502, when the locking member 532 is in a second, locked position. As will be discussed, in a first, unlocked position, the cap 530 can rotate relative to the saddle 502 to enable an operator to select a single desired plane for the planar movement of the bone fastener 304.

It should be noted, however, that the locking member 532, cap locking portion 536 and locking portion 518 of the saddle 502 can have any suitable configuration in which the locking member 532 can be moved to prevent the rotation of the cap 530 relative to the saddle 502. In one example, with reference to FIG. 40, a locking member 532c can comprise a ring having a rectangular interior planar surface 532d and the exterior teeth 532b. In this example, a cap 530c can include a rectangular projection 534c and a rectangular planar cap locking portion 536c. The interior planar surface 532d of the locking member 532c can mate with the rectangular planar cap locking portion 536c of the cap 530c to couple the cap 530c to the locking member 532c.

Figure 41:
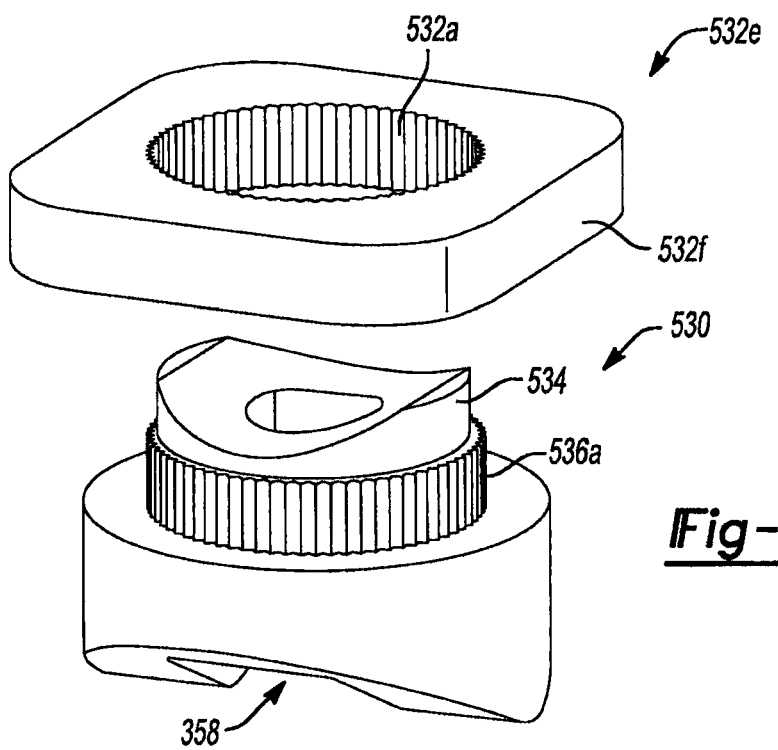
FIG. 41 is an exploded, perspective view of another exemplary locking member and cap for use with the uniplanar bone anchor system of FIG. 36.

In a second example, with reference to FIG. 41, a locking member 532e can comprise a rectangular ring having the interior teeth 532a and a planar exterior surface 532f. In this example, a locking portion of a saddle can comprise a rectangular planar surface, which can extend about an interior periphery of the saddle 502. The planar exterior surface 532f of the locking member 532e can mate with the square planar locking portion of the saddle to prevent the rotation of the cap 530 relative to the saddle 502.

With reference back to FIGS. 37, 42 and 43, in order to assemble the bone anchor system 500, the support ring 352 can be coupled to the groove 344 of the bone fastener 304. Then, the bone fastener 304 can be coupled to the saddle 502. Once the bone fastener 304 is coupled to the saddle 502, the cap 530 can be rotated within the saddle 502 with a suitable instrument until a desired single plane is selected for the rotation of the bone fastener 304. Next, the supports 354 can be coupled to the bone fastener 304 via the engagement of the channel 378a with the support ring 352. The cap 530 can be positioned within the central bore 312 of the saddle 502, such that the cap 530 is in contact with the teeth 536a of the cap locking portion 536. With the cap 530 positioned within the central bore 312, the locking member 532 can be inserted between the first arm 512 and second arm 514.

In the first, unlocked position (FIG. 42), the locking member 532 can be adjacent to the notches 516 of the first arm 512 and second arm 514. The locking member 532 can slide or rotate relative to the saddle 502 to allow the cap 530 to rotate relative to the saddle 502. An operator can move the saddle 502 until the bone fastener 304 is aligned with the desired single plane of motion. Then, the operator can move the locking member 532 into a second, locked position (FIG. 43) so that the interior teeth 532a engage the teeth 536a of the cap locking portion 536, and the exterior teeth 532b engage the teeth 518a of the locking portion 518 of the saddle 502 to prevent the rotation of the cap 530 relative to the saddle 502.

Thus, the bone anchor system 500 can enable an operator to select a desired single plane of motion for the saddle 502 relative to the bone fastener 304, which can enable the operator to customize the bone anchor system 500 for the particular patient. As the surgical insertion and use of the bone anchor system 500 in a fixation procedure can be similar to the surgical insertion and insertion of the bone anchor system 300 in a fixation procedure, the surgical insertion and use of the bone anchor system 500 need not be discussed in great detail herein.

Figure 44:
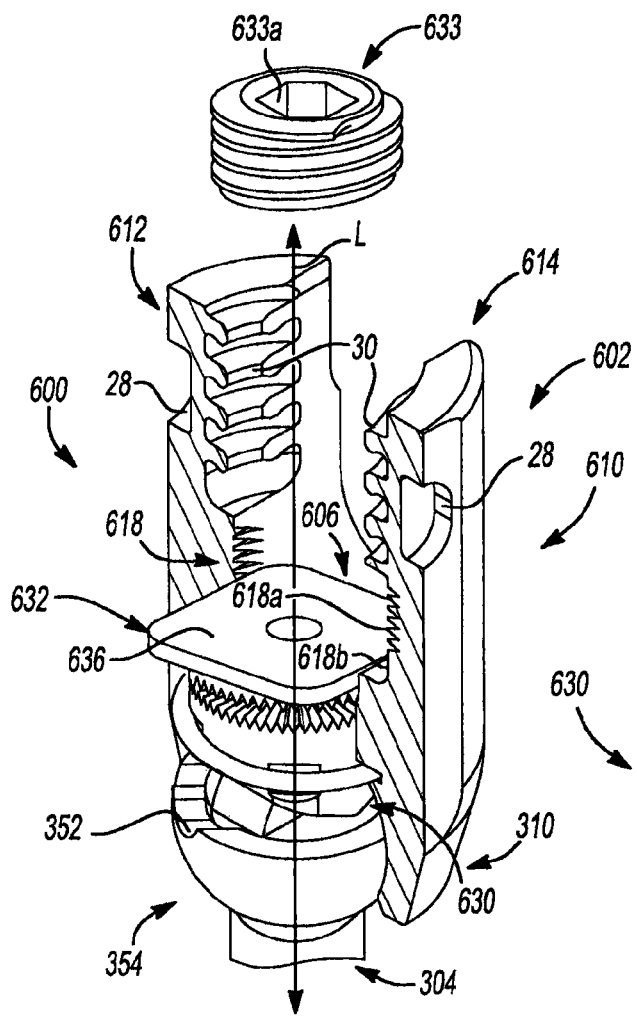
FIG. 44 is a schematic cross-sectional illustration of another exemplary uniplanar bone anchor system for use with a connecting device in a fixation procedure according to the present teachings.
Figure 45:
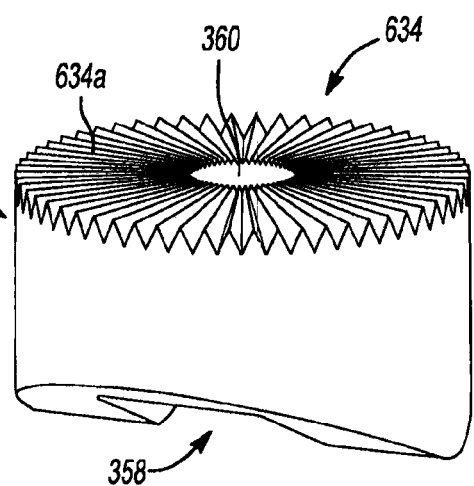
FIG. 45 is a perspective view of an exemplary cap for use with the uniplanar bone anchor system of FIG. 44.
Figure 46:
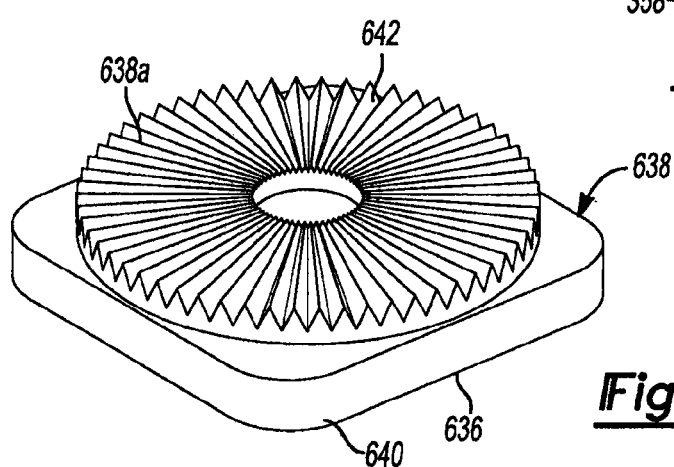
FIG. 46 is a perspective view of an exemplary locking member for use with the uniplanar bone anchor system of FIG. 44.

With reference now to FIGS. 44-46, in one example, a bone anchor system 600 can be employed with the connecting rod 18 to repair a damaged portion of an anatomy. As the bone anchor system 600 can be similar to the bone anchor system 300 described with reference to FIGS. 25-30, only the differences between the bone anchor system 300 and the bone anchor system 600 will be discussed in great detail herein, and the same reference numerals will be used to denote the same or similar components. The bone anchor system 600 can include a saddle 602, the bone fastener 304 and a uniplanar coupling system 606.

The saddle 602 can be substantially U-shaped and symmetrical with respect to a longitudinal axis L defined by the bone anchor system 600. The saddle 602 can include a first or proximal end 610 and the distal end 310. The proximal end 610 can include a first arm 612 and a second arm 614. The first arm 612 and second arm 614 can extend upwardly from the distal end 310 to define the U-shape. Each of the first arm 612 and the second arm 614 can include the insertion feature 28, the mating portion 30 and a locking portion 618. The mating portion 30 can be formed on an interior surface 612a, 614a, of each of the first arm 612 and second arm 614, respectively.

The locking portion 618 can be formed between the proximal end 610 and the distal end 310. In one example, the locking portion 618 can be defined about a circumference of the proximal end 610, adjacent to the distal end 310. The locking portion 618 can include a threaded portion 618a and a planar portion 618b. Each of the threaded portion 618a and the planar portion 618b can mate with a portion of the coupling system 606 to prevent the rotation of a portion of the coupling system 606 relative to the saddle 602.

The coupling system 606 can comprise a cap 630, a locking member 632, a fastener 633, the support ring 352 and the supports 354. The cap 630 can be substantially symmetrical about the longitudinal axis L, and can be received within the rectangular portion of the central bore 312. The cap 630 can be composed of any suitable biocompatible material, such as a biocompatible metal, metal alloy and/or polymer. With reference to FIG. 45, the cap 630 can include a top surface 634, the bottom surface 358 and the aperture 360.

The top surface 634 can be opposite the bottom surface 358. The top surface 634 can include a plurality of grooves or serrations 634a. The serrations 634a can extend radially from the aperture 360, and can be formed about a circumference of the top surface 634. The serrations 634a can mate with a portion of the locking member 632 to prevent the rotation of the cap 630 relative to the saddle 602.

In this regard, with reference to FIG. 46, the locking member 632 can comprise a rectangular plate, which can be received between the first arm 612 and second arm 614 of the saddle 602. The locking member 632 can include a first or top surface 636, a second or bottom surface 638, a periphery 640 and a bore 642, which can extend from the top surface 636 to the bottom surface 638.

The top surface 636 can be generally smooth, and can be opposite the bottom surface 638. The bottom surface 638 can include a plurality of grooves or serrations 638a. The serrations 638a can extend radially from the bore 642, and can be formed about a circumference of the bottom surface 636. The serrations 638a can mate with the serrations 634a of the cap 630. The periphery 640 can be substantially planar, and can be sized to be positioned adjacent to the planar portion 618b of the saddle 602 to prevent the rotation of the cap 630 relative to the saddle 602 when the locking member 632 is in a second, locked position. The bore 642 can enable an instrument to pass through the coupling system 606 to couple the bone fastener 304 to the anatomy.

With reference to FIG. 44, the fastener 633 can move the locking member 632 from a first, unlocked position to the second, locked position. It should be understood, however, that the fastener 633 can be optional, as the locking member 632 could be placed into engagement with the cap 630 through any suitable technique. The fastener 633 can include a plurality of threads 633a. If employed, the fastener 633 can be inserted between the first arm 612 and second arm 614 so that the threads 633a can engage the threaded portion 618a of the saddle 602. The advancement of the fastener 633 within the saddle 602 can move or advance the locking member 632 from the first, unlocked position to the second, locked position. As will be discussed, in the first, unlocked position, the cap 630 can rotate relative to the saddle 602 to enable an operator to select a single desired plane for the planar movement of the bone fastener 304.

In order to assemble the bone anchor system 600, the support ring 352 can be coupled to the groove 344 of the bone fastener 304. Then, the bone fastener 304 can be coupled to the saddle 602. Next, the supports 354 can be coupled to the bone fastener 304. The cap 630 can be positioned within the central bore 312 of the saddle 602, such that the cap 630 is in contact with the rectangular portion of the central bore 312. With the cap 630 positioned within the central bore 312, the locking member 632 can be inserted between the first arm 612 and second arm 614 such that the locking member 632 is adjacent to the threaded portion 618a of the saddle 602.

With the locking member 632 in the first, unlocked position, the locking member 632 can be positioned adjacent to the threaded portion 618a of the first arm 512 and second arm 514. An operator can move the saddle 602 until the saddle 602 is aligned with the desired single plane of motion. Then, the operator can insert the fastener 633 into the saddle 602. Using a suitable instrument, the fastener 633 can be advanced to engage the threads 633a of the fastener 633 with the threaded portion 618b of the saddle 602. The engagement of the fastener 633 with the threaded portion 618b can move the locking member 632 from the first, unlocked position to the second, locked position. In the second, locked position, the serrations 638a of the locking member 632 can be meshingly engaged with the serrations 634a of the cap 630 to prevent the rotation of the cap 630 relative to the saddle 602.

Thus, the bone anchor system 600 can enable an operator to select a desired single plane of motion for the saddle 602 relative to the bone fastener 304, which can enable the operator to customize the bone anchor system 600 for the particular patient. As the surgical insertion and use of the bone anchor system 600 in a fixation procedure can be similar to the surgical insertion and insertion of the bone anchor system 300 in a fixation procedure, the surgical insertion and use of the bone anchor system 600 need not be discussed in great detail herein.

Accordingly, the bone anchor system 10, 100, 200, 300, 400, 500, 600 can be used to repair damaged tissue in the anatomy, such as in the case of a spinal fixation or fusion procedure. By allowing the saddle 12, 202, 302, 502, 602 to move relative to the bone fastener 14, 204, 304 in only one plane, the surgeon can align the saddles 12, 202, 302, 502, 602 to allow for easier insertion of the connecting rod 18. In addition, the ability to select the single plane of motion for the bone fastener 304 can enable the bone anchor system 500, 600 to be used with a variety of different anatomical structures.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

For example, while the bone anchor system 10 has been described herein as having an optional pressure cap 17 that has a smooth concave bottom surface 62, those of skill in the art will appreciate that the present disclosure, in its broadest aspects, may be constructed somewhat differently. In this regard, with reference to FIG. 47, the pressure cap 17 could include a plurality of teeth 17a and/or a plurality of teeth 17b. The teeth 17a can bite into the first bearing surface 56a and the second bearing surface 56b of the head 56 of the bone fastener 14 to further control the rotation of the bone fastener 14 relative to the saddle 12. The plurality of teeth 17b can provide an additional locking or frictional force for coupling the connecting rod 18 to the bone anchor system 10.

As a further example, with reference to FIG. 48, the first bearing surface 56a and the second bearing surface 56b of the head 56 of the bone fastener 14 could each include a plurality of teeth 700. The plurality of teeth 700 can bite into the smooth bottom surface 62 of the pressure cap 17 or can engage the teeth 17a of the pressure cap 17 to further control the rotation of the bone fastener 14. If the pressure cap 17 is not employed, then the teeth 700 of the bone fastener 14 can bite into the connecting rod 18 to provide an additional coupling force to the connecting rod 18.

What is claimed is:

1. A uniplanar bone anchor system for a fixation procedure comprising:
 a bone fastener including a head and a shaft adapted to engage an anatomy, the head having at least one first bearing surface;
 a saddle having a proximal end and a distal end, the distal end including a first bore formed about the longitudinal axis that receives the head of the bone fastener;
 a coupling system including a cap and at least one annular support, the cap defining at least one second bearing surface configured to allow the bone fastener to move in one plane relative to the saddle, the at least one annular support coupled to the head of the bone fastener to retain the bone fastener within the first bore; and
 wherein the cap is received within the first bore such that the at least one second bearing surface of the cap contacts the at least one first bearing surface of the head to permit the bone fastener to move relative to the saddle in the one plane; and
 the head defines a slot that extends through a portion of the first bearing surface, and the cap includes at least one triangular projection that is received into the slot to restrict the movement of the bone fastener to the one plane.

2. The system of claim 1, wherein the first bore defines a planar portion and an arcuate portion, the cap being received within the planar portion and the at least one annular support being received within the arcuate portion, the cap and the at least one annular support cooperating with the first bore and the bone fastener to limit the movement of the bone fastener relative to the saddle.

3. The system of claim 2, wherein the cap is movable relative to the planar portion of the first bore to enable selection of the one plane.

4. The system of claim 1, wherein the at least one annular support comprises two annular supports, which are each coupled to the bone fastener to substantially surround the head of the bone fastener.

5. A uniplanar bone anchor system for a fixation procedure comprising:
   a bone fastener including a head and a shaft adapted to engage an anatomy, the head having at least one first bearing surface;
   a saddle including a bore formed about a longitudinal axis that receives the head of the bone fastener;
   a coupling system including a cap, at least one annular support, and a support ring, the cap defining at least one second bearing surface configured to allow the bone fastener to move in one plane relative to the saddle, the at least one annular support disposed about the head of the bone fastener to retain the bone fastener within the bore, and the support ring disposed between the at least one annular support and the head to secure the at least one annular support to the head; and
   wherein the cap is received within the bore such that the at least one second bearing surface of the cap contacts the at least one first bearing surface of the head to permit the bone fastener to move relative to the saddle in the one plane.

6. The system of claim 5, wherein the head includes a projection that defines the first bearing surface, and the cap includes a pair of spaced-apart triangular projections that receive the projection of the head to restrict the movement of the bone fastener to the one plane.

7. The system of claim 5, wherein head includes a pair of first bearing surfaces separated by slot, and the cap includes a projection configured to be received in the slot to restrict the movement of the bone fastener to the one plane.

8. The system of claim 5, wherein the head includes an annular groove for receiving the support ring.

9. The system of claim 8, wherein the at least one annular support includes a channel for receiving the support ring.

10. The system of claim 5, wherein the saddle comprises a first locking portion and the cap defines a second locking portion, the system further comprising:
    a locking member that in a first position is uncoupled from the first locking portion and the second locking portion to enable the cap to be rotated relative to the saddle, and in a second position, the locking member cooperates with at least one of the first locking portion and the second locking portion to prevent the rotation of the cap relative to the saddle.

11. The system of claim 10, wherein each of first locking portion, the second locking portion, and the locking member include a plurality of teeth.

12. The system of claim 11, wherein the locking member is annular and includes first teeth and second teeth, the first teeth intermeshing with the teeth of the first locking portion and the second teeth intermeshing with teeth of the second locking portion to prevent rotation of the cap relative to the saddle.

* * * * *